(12) United States Patent
Morooka

(10) Patent No.: US 9,994,661 B2
(45) Date of Patent: Jun. 12, 2018

(54) CURABLE COMPOSITION, CURED PRODUCT, OPTICAL COMPONENT, LENS, AND COMPOUND

(71) Applicant: FUJIFILM Corporation, Tokyo (JP)

(72) Inventor: Naoyuki Morooka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/678,614

(22) Filed: Aug. 16, 2017

(65) Prior Publication Data

US 2017/0342181 A1 Nov. 30, 2017

Related U.S. Application Data

(63) Continuation of application No. PCT/JP2016/056365, filed on Mar. 2, 2016.

(30) Foreign Application Priority Data

Mar. 2, 2015 (JP) .................................. 2015-040032
Dec. 25, 2015 (JP) .................................. 2015-253519

(51) Int. Cl.
| | |
|---|---|
| C08F 2/46 | (2006.01) |
| C08G 61/04 | (2006.01) |
| C08F 220/30 | (2006.01) |
| C07C 69/602 | (2006.01) |
| C07C 69/96 | (2006.01) |
| C07C 217/94 | (2006.01) |
| G02B 1/04 | (2006.01) |

(52) U.S. Cl.
CPC .......... *C08F 220/30* (2013.01); *C07C 69/602* (2013.01); *C07C 69/96* (2013.01); *C07C 217/94* (2013.01); *G02B 1/041* (2013.01); *C08F 2220/305* (2013.01)

(58) Field of Classification Search
None
See application file for complete search history.

(56) References Cited

U.S. PATENT DOCUMENTS

| | | |
|---|---|---|
| 2010/0201925 A1 | 8/2010 | Kim et al. |
| 2012/0251948 A1 | 10/2012 | Iizuka et al. |
| 2015/0197592 A1 | 7/2015 | Someya et al. |

FOREIGN PATENT DOCUMENTS

| | | | | |
|---|---|---|---|---|
| CN | 102659526 | * | 8/2014 | |
| JP | 2008-094987 A | | 4/2008 | |
| JP | 2008081418 | * | 4/2008 | ....... A61K 47/48415 |
| JP | 2010-523756 A | | 7/2010 | |
| JP | 2011-068624 A | | 4/2011 | |
| JP | 2013-061624 A | | 4/2013 | |
| JP | 2014-080572 A | | 5/2014 | |
| WO | WO-2012147712 A1 | * | 11/2012 | ............... C09D 4/00 |
| WO | WO-2017146023 | * | 2/2016 | |

OTHER PUBLICATIONS

Hansch et al, A survey of Hammett Substituent Constants and Resonance and Field Parameters, 1991, Chem. Rev., 91, 165-195 (Year: 1991).*
Ito et al, JP 2008-081418 Machine Translation, Apr. 10, 2008 (Year: 2008).*
Motoharu et al, WO 2012147712 Machine Translation, Nov. 1, 2012 (Year: 2012).*
Junting et al, CN 102659526 Machine Translation, Aug. 20, 2014 (Year: 2014).*
Uehira et al, WO 2017146023 Machine Translation, Feb. 24, 2016 (Year: 2016).*
International Preliminary Report on Patentability dated Sep. 5, 2017 in counterpart international Application No. PCT/JP2016/056365.
Translation of Written Opinion of the International Searching Authority dated May 24, 2016 in counterpart international Application No. PCT/JP2016/056365.

* cited by examiner

*Primary Examiner* — Jessica Whiteley
(74) *Attorney, Agent, or Firm* — Sughrue Mion, PLLC

(57) ABSTRACT

Disclosed herein are a curable composition which is capable of producing a cured product having a low Abbe's number and increased durability, and a curable composition with suppressed viscosity increase. Provided is a compound represented by General Formula (A). Also provided are a curable composition including a compound represented by General Formula (A), a predetermined (meth)acrylate monomer, and at least one selected from a photoradical polymerization initiator and a thermal radical polymerization initiator; a cured product formed by curing the curable composition; an optical component; and a lens.

General Formula (A)

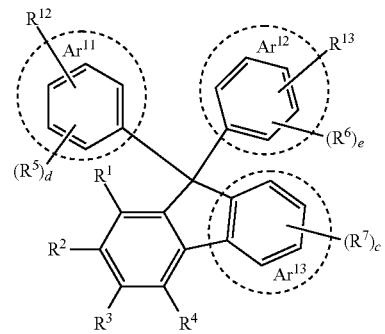

25 Claims, 5 Drawing Sheets

CURABLE COMPOSITION, CURED PRODUCT, OPTICAL COMPONENT, LENS, AND COMPOUND

CROSS-REFERENCE TO RELATED APPLICATIONS

This application is a Continuation of PCT International Application No. PCT/JP2016/056365, filed on Mar. 2, 2016, which claims priority under 35 U.S.C. Section 119(a) to Japanese Patent Application No. 2015-040032 filed on Mar. 2, 2015, and Japanese Patent Application No. 2015-253519 filed on Dec. 25, 2015. Each of the above applications is hereby expressly incorporated by reference, in its entirety, into the present application.

BACKGROUND OF THE INVENTION

1. Field of the Invention

The present invention relates to a curable composition, a cured product, an optical component, a lens, and a compound.

2. Description of the Related Art

Conventionally, a glass material has been used for an optical component of an imaging module such as a camera, a cellular phone with a video camera or a camera, and a door phone with a video telephone or a camera. The glass material has been preferably used since it has various optical properties and excellent environmental resistance, but has a disadvantage in that weight reduction and miniaturization are not easy and workability or productivity is not good. In contrast, since a resin cured product can be produced in a massive amount and has excellent workability, the resin cured product has recently been used in various optical components.

In recent years, along with the miniaturization of an imaging module, it has been required to downsize an optical component used in the imaging module. However, miniaturization of the optical component brings about a problem associated with the chromatic aberration. In an optical component using a resin cured product, it has been studied to correct chromatic aberration by decreasing the Abbe's number through the addition of various additives to a curable composition to thereby change post-curing properties thereof.

As a monomer used in a curable composition for producing an optical component, a compound having a fluorene skeleton is used. For example, JP2011-68624A discloses a method for producing an alcohol, epoxy, or (meth)acrylate having a fluorene skeleton. Here, a (meth)acrylate having a 9,9-bisphenylfluorene skeleton and a (meth)acrylate having a 9,9-bisnaphthylfluorene skeleton have been disclosed.

In addition, JP2014-80572A discloses a cardo skeleton-containing compound having a fused ring at a predetermined position as a monomer used in a curable composition.

SUMMARY OF THE INVENTION

However, it has been demonstrated through studies conducted by the present inventors that in the case where the compound disclosed in JP2011-68624A is used in a curable composition, the reduction in the Abbe's number is not sufficient, and furthermore, in the case where it is made into a resin cured product (hereinafter, referred to as a cured product), its durability is poor. Further, in the case where the compound disclosed in JP2014-80572A is used in a curable composition, there is a problem that in the case where it is attempted to suppress the Abbe's number, the viscosity of the curable composition becomes higher, and consequently the working efficiency in the case of producing a cured product cannot be sufficiently enhanced.

Therefore, in order to solve such problems of the related art, the present inventors have studied for the purpose of providing a curable composition and a compound which is capable of producing a cured product having a low Abbe's number and increased durability. Further, the present inventors have also studied for the purpose of providing a curable composition and a compound with suppressed viscosity increase even in the case of producing a cured product having a low Abbe's number.

Specific means for achieving the objects are as follows.

[1] A curable composition comprising a compound represented by General Formula (A), a (meth)acrylate monomer having a viscosity at 25° C. of less than 2,000 mPa·s, and at least one selected from a photoradical polymerization initiator and a thermal radical polymerization initiator,

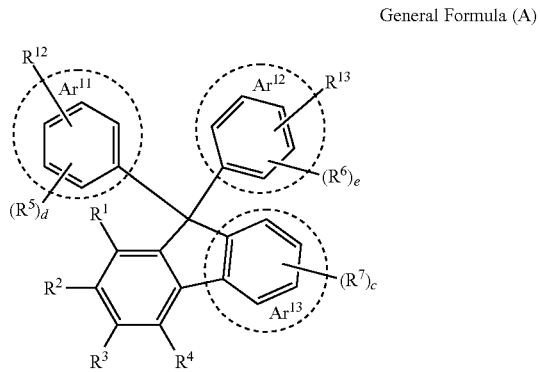

General Formula (A)

in General Formula (A), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $R^{12}$ and $R^{13}$ are each independently a hydroxyl group, a mercapto group, an amino group, or a group having a polymerizable unsaturated bond; c to e each independently represent an integer of 0 to 4; in a case where $Ar^{11}$ and $Ar^{12}$ are each independently an aromatic fused ring group containing a benzene ring surrounded by a broken line as one of the fused rings, $R^5$, $R^6$, $R^{12}$, and $R^{13}$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

[2] The curable composition according to [1], in which the compound is a compound represented by General Formula (1), General Formula (1)

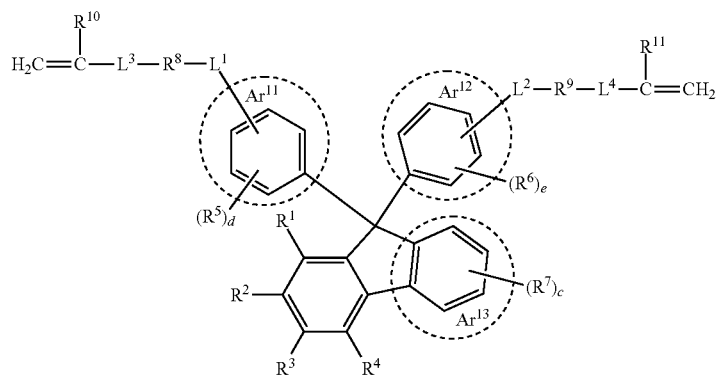

in General Formula (1), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; in the case where $Ar^{11}$ and $Ar^{12}$ each independently represent an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

[3] The curable composition according to [1] or [2], in which the compound is a compound represented by General Formula (2), General Formula (2)

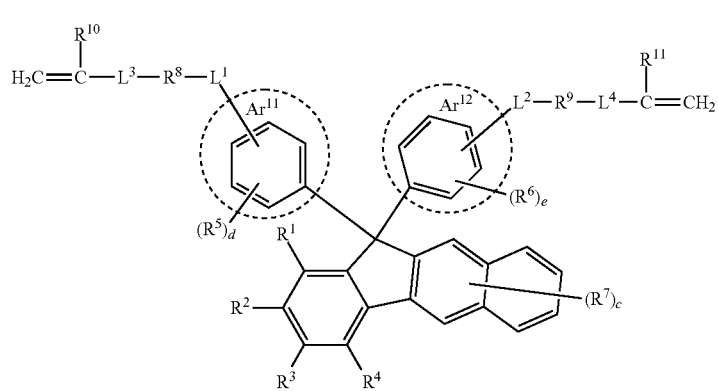

in General Formula (2), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; and in the case where $Ar^{11}$ and $Ar^{12}$ are each independently an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line.

[4] The curable composition according to any one of [1] to [3], in which at least one of $R^2$ or $R^4$ is a substituent having a Hammett substituent constant $\sigma_p$ value of smaller than $-0.15$.

[5] The curable composition according to any one of [1] to [4], in which at least one of $R^1$, $R^2$, $R^3$, or $R^4$ is an alkyl group, an alkoxy group, or a dialkylamino group.

[6] The curable composition according to any one of [1] to [5], in which at least one of $R^1$, $R^2$, $R^3$, or $R^4$ is an alkoxy group.

[7] The curable composition according to any one of [1] to [6], in which at least one of $R^2$ or $R^4$ is an alkoxy group.

[8] The curable composition according to any one of [1] to [7], in which at least one of $R^2$ or $R^4$ is an alkoxy group, and at least two of $R^1$, $R^2$, $R^3$, or $R^4$ are alkoxy groups.

[9] The curable composition according to any one of [1] to [8], in which $R^2$ and $R^3$ are alkoxy groups.

[10] The curable composition according to any one of [5] to [9], in which the alkoxy group is a methoxy group.

[11] The curable composition according to any one of [1] to [10], in which the viscosity at 25° C. of the (meth)acrylate monomer is less than 500 mPa·s.

[12] The curable composition according to any one of [1] to [11], in which the (meth)acrylate monomer is a (meth)acrylate monomer containing an aryl group or a heteroaryl group.

[13] The curable composition according to any one of [1] to [12], in which the content of the compound in the curable composition is 20 to 94 mass %, the content of the (meth)acrylate monomer is 5 to 80 mass %, and the content of at least one selected from a photoradical polymerization initiator and a thermal radical polymerization initiator is 0.01 to 10 mass %.

[14] A cured product of the curable composition according to any one of [1] to [13].

[15] An optical component comprising the cured product according to [14].

[17] A lens comprising the cured product according to [14].

[17] A compound represented by General Formula (A),

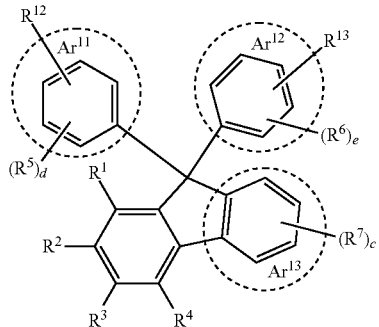

General Formula (A)

in General Formula (A), at least one of $R^1$, $R^2$, $R^3$, or $R^4$ is a substituent having a Hammett substituent constant $\sigma_p$ value of smaller than $-0.15$, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $R^{12}$ and $R^{13}$ are each independently a hydroxyl group, a mercapto group, an amino group, or a group having a polymerizable unsaturated bond; c to e each independently represent an integer of 0 to 4; in the case where $Ar^{11}$ and $Ar^{12}$ are each independently an aromatic fused ring group containing a benzene ring surrounded by a broken line as one of the fused rings, $R^5$, $R^6$, $R^{12}$, and $R^{13}$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

[18] The compound according to [17], in which the compound is represented by General Formula (1),

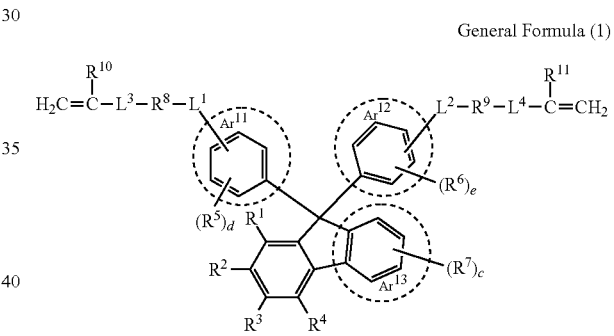

General Formula (1)

in General Formula (1), at least one of $R^1$, $R^2$, $R^3$, or $R^4$ is a substituent having a Hammett substituent constant $\sigma_p$ value of smaller than $-0.15$, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; in the case where $Ar^{11}$ and $Ar^{12}$ each independently represent an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

[19] The compound according to [17] or [18], in which the compound is represented by General Formula (2),

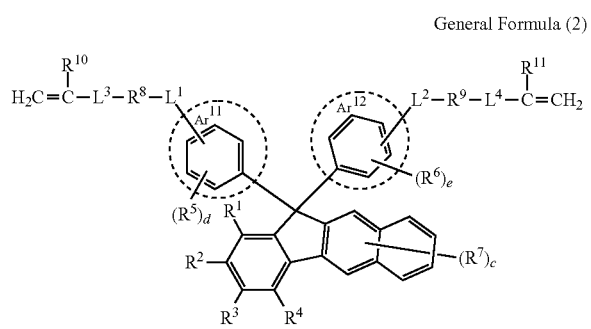

General Formula (2)

in General Formula (2), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; and in the case where $Ar^{11}$ and $Ar^{12}$ are each independently an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line.

[20] The compound according to any one of [17] to [19], in which at least one of $R^1$, $R^2$, $R^3$, or $R^4$ is an alkyl group, an alkoxy group, or a dialkylamino group.

[21] The compound according to any one of [17] to [20], in which at least one of $R^1$, $R^2$, $R^3$, or $R^4$ is an alkoxy group.

[22] The compound according to any one of [17] to [21], in which at least one of $R^2$ or $R^4$ is an alkoxy group.

[23] The compound according to any one of [17] to [22], in which at least one of $R^2$ or $R^4$ is an alkoxy group, and at least two of $R^1$, $R^2$, $R^3$, or $R^4$ are alkoxy groups.

[24] The compound according to any one of [17] to [23], in which $R^2$ and $R^3$ are alkoxy groups.

[25] The compound according to any one of [20] to [24], in which the alkoxy group is a methoxy group.

According to the present invention, it is possible to obtain a curable composition which is capable of producing a cured product having a low Abbe's number and enhanced durability. Further, according to the present invention, it is possible to obtain a curable composition with suppressed viscosity increase even in the case of producing a cured product having a low Abbe's number.

DESCRIPTION OF THE PREFERRED EMBODIMENTS

Figure 1:
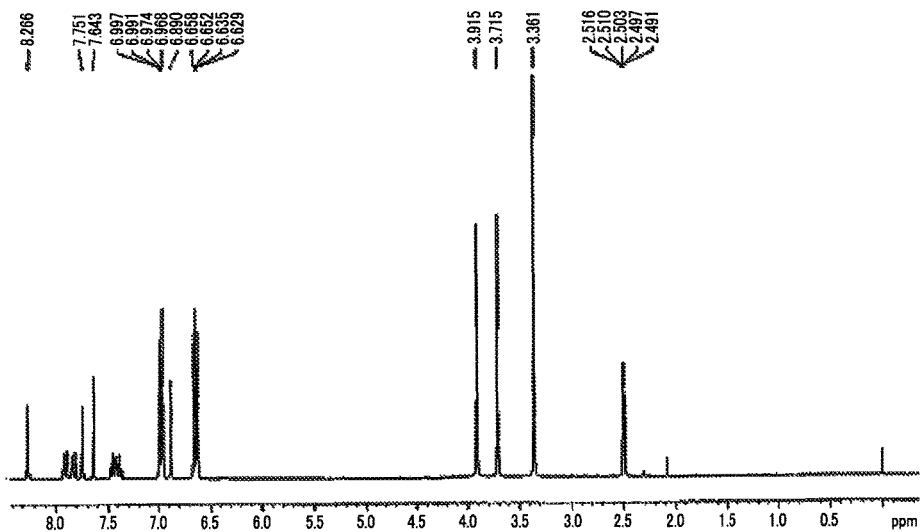
FIG. 1 is a $^1$H-Nuclear Magnetic Resonance (NMR) chart of Compound 2-1B.

Hereinafter, the present invention will be described in detail. The description of constituent elements described below can be made based on representative embodiments and specific examples, but the present invention is not limited to such embodiments. Numerical ranges expressed using "to" in the present specification mean a range including numerical values described before and after "to" as the lower limit and the upper limit.

In the present specification, "(meth)acrylate" refers to acrylate and methacrylate, "(meth)acrylic" refers to acrylic and methacrylic, and "(meth)acryloyl" refers to acryloyl and methacryloyl. The monomer in the present invention is a compound distinguished from oligomers and polymers and having a weight-average molecular weight of 1,000 or less.

In the indication of a group (atomic group) in the present specification, the indication not including substitution or unsubstitution includes those having a substituent and also those not having a substituent. For example, an "alkyl group" refers not only to an alkyl group not having a substituent (unsubstituted alkyl group) but also an alkyl group having a substituent (substituted alkyl group).

(Curable Composition)

The present invention relates to a curable composition including a compound represented by General Formula (A) to be described below, a (meth)acrylate monomer having a viscosity at 25° C. of less than 2,000 mPa·s, and at least one selected from a photoradical polymerization initiator and a thermal radical polymerization initiator. The compound is preferably a compound represented by General Formula (1) or General Formula (2) to be described below.

Since the curable composition of the present invention contains a compound having a specific structure and the predetermined components as described above, it is possible to form a cured product having a low Abbe's number and enhanced durability. Further, the curable composition of the present invention has both of a property that a cured product having a low Abbe's number can be formed and a property that an increase in viscosity is suppressed. The curable composition in which an increase in viscosity is suppressed has good handleability in the case of forming a cured product and can enhance work efficiency in forming a cured product. Further, in the case where a cured product is formed using a curable composition in which an increase in viscosity is suppressed, it becomes easier to prepare a cured product of high quality and the yield at the time of forming a cured product can be improved.

It is preferred that the content of the compound in the curable composition is 20 to 94 mass %, the content of the (meth)acrylate monomer is 5 to 80 mass %, and the content of at least one selected from a photoradical polymerization initiator and a thermal radical polymerization initiator is 0.01 to 10 mass %. A more preferred content of each component will be described in individual items described below.

The viscosity of the curable composition of the present invention is preferably 20,000 mPa·s or less, more preferably 15,000 mPa·s or less, still more preferably 13,000 mPa·s or less, even still more preferably 11,900 mPa·s or less, and particularly preferably 10,000 mPa·s or less. As described above, since the curable composition of the present invention has a low viscosity, a handleability at the time of forming a cured product can be enhanced and a cured product of high quality can be formed.

(Compound Represented by General Formula (A))

The curable composition of the present invention includes a compound represented by General Formula (A). The compound represented by General Formula (A), as shown below, is a fused ring-containing compound. Further, the present invention also relates to a compound which will be described below.

General Formula (A)

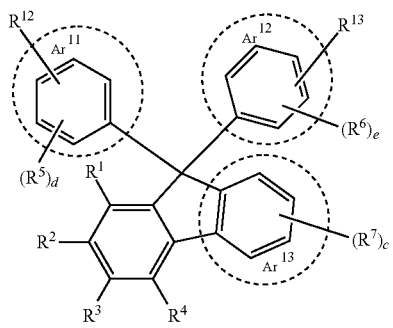

In General Formula (A), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $R^{12}$ and $R^{13}$ are each independently a hydroxyl group, a mercapto group, an amino group, or a group having a polymerizable unsaturated bond; c to e each independently represent an integer of 0 to 4; in the case where $Ar^{11}$ and $Ar^{12}$ are each independently an aromatic fused ring group containing a benzene ring surrounded by a broken line as one of the fused rings, $R^5$, $R^6$, $R^{12}$, and $R^{13}$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

In General Formula (A), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring. Here, the reactive group is a (meth)acryloyl group.

At least one of $R^1$, $R^2$, $R^3$, or $R^4$ is a substituent having a Hammett substituent constant $\sigma_p$ value of smaller than −0.15. When at least one of $R^1$, $R^2$, $R^3$, or $R^4$ is an electron donating group having a Hammett substituent constant $\sigma_p$ within the above-specified range, it is possible to lower the Abbe's number of a cured product. This is considered to be because the ultraviolet absorption of the compound is shifted to the long wavelength side by the electron donating group and the wavelength dependency of the refractive index in the visible light region is strengthened, thereby making it possible to reduce the Abbe's number.

The Hammett substituent constant $\sigma_p$ value is more preferably −0.20 or less and still more preferably −0.25 or less. The lower limit value of the Hammett substituent constant $\sigma_p$ value is preferably −0.7.

Hammett substituent constant $\sigma_p$ values are described in Correlation Analysis in Chemistry, Ed. By N. B. Chapman, J. Shorter, pp. 439 to 540, Plenum Press (1978) and the references cited therein. Here, $\sigma_p$ is defined as follows.

$$\sigma_p = \mathrm{Log}(Ka/Ka^0) = pKa^0 - pKa$$

$Ka^0$ is the acid dissociation constant of benzoic acid at 25° C. in water. $Ka$ is the acid dissociation constant of para-substituted benzoic acid at 25° C. in water. Note that those not described in the above document can be determined according to the method described in the same document.

Examples of the substituent having a Hammett substituent constant $\sigma_p$ value of smaller than −0.15 include a cyclopropyl group (-cycloC$_3$H$_5$, $\sigma_p$ value of −0.21), an amino group (—NH$_2$, $\sigma_p$ value of −0.57), a dimethylamino group (—N(CH$_3$)$_2$, $\sigma_p$ value of −0.63), a benzoylamino group (—NHCOC$_6$H$_5$, $\sigma_p$ value of −0.19), a hydroxyl group (—OH, $\sigma_p$ value of −0.38), a methoxy group (—OCH$_3$, $\sigma_p$ value of −0.28), an ethoxy group (—OC$_2$H$_5$, $\sigma_p$ value of −0.21), and a propoxy group (—OC$_3$H$_7$, $\sigma_p$ value of −0.25). In the case where a plurality of substituents out of $R^1$ to $R^4$ are a substituent having a Hammett substituent constant $\sigma_p$ value of smaller than −0.15, these substituents may be the same or different.

In General Formula (A), at least one of $R^2$ or $R^4$ is preferably a substituent having a Hammett substituent constant $\sigma_p$ value of smaller than −0.15. By making the Hammett substituent constant $\sigma_p$ value of the substituent disposed at a specific position smaller than −0.15 as described above, it is possible to more effectively lower the Abbe's number of a cured product.

Further, in General Formula (A), at least one of $R^1$, $R^2$, $R^3$, or $R^4$ is preferably an alkyl group, an alkoxy group, or a dialkylamino group. In this case, the alkyl group, alkoxy group, or dialkylamino group which can be selected by at least one of $R^1$, $R^2$, $R^3$, or $R^4$ is a group having a Hammett substituent constant $\sigma_p$ value of smaller than −0.15. Among them, at least one of $R^1$, $R^2$, $R^3$, or $R^4$ is preferably an alkoxy group, more preferably a methoxy group, an ethoxy group or a propoxy group, and still more preferably a methoxy group.

By setting at least one of $R^1$, $R^2$, $R^3$, or $R^4$ to be an alkoxy group as described above, the structure of the compound represented by General Formula (A) becomes more compact and the ultraviolet absorption of the compound can be shifted to the longer wavelength side. Thereby, the Abbe's number of a cured product can be effectively reduced. Further, by setting at least one of $R^1$, $R^2$, $R^3$, or $R^4$ to be an alkoxy group, the coloring of a cured product can be suppressed.

It is preferred that at least one of $R^2$ or $R^4$ is an alkoxy group. Further, it is more preferred that at least one of $R^2$ or $R^4$ is an alkoxy group, and at least two of $R^1$, $R^2$, $R^3$, or $R^4$ are alkoxy groups. That is, it is preferred that in General Formula (A), two or more groups of $R^1$ to $R^4$ are alkoxy groups, one of which is preferably in the position of $R^2$ or $R^4$.

A preferred combination of the positions having an alkoxy group is, for example, $R^2$ and $R^1$, $R^2$ and $R^3$, $R^2$ and $R^4$, $R^1$ and $R^4$, or $R^3$ and $R^4$, preferably $R^2$ and $R^3$ or $R^2$ and $R^4$, and more preferably $R^2$ and $R^3$. By setting the combination of the positions having an alkoxy group to $R^2$ and $R^3$ or $R^2$ and $R^4$, the electron donating effect is easily obtained, and the Abbe's number of a cured product can be more effectively reduced. Among them, the combination of $R^2$ and $R^3$ is preferably used because the synthesis of the compound is easy.

In General Formula (A), $R^5$ to $R^7$ each independently represent a substituent. The substituent represented by $R^5$ to $R^7$ is not particularly limited, and examples thereof include a halogen atom, a halogenated alkyl group, an alkyl group, an alkenyl group, an acyl group, a hydroxyl group, a hydroxyalkyl group, an alkoxy group, an aryl group, a heteroaryl group, and an alicyclic group. The substituent represented by $R^5$ to $R^7$ is preferably an alkyl group, an alkoxy group, or an aryl group, more preferably an alkyl group having 1 to 5 carbon atoms, an alkoxy group having 1 to 5 carbon atoms, or a phenyl group, and particularly preferably a methyl group, a methoxy group, or a phenyl group. In General Formula (A), in the case where $Ar^{11}$ and $Ar^{12}$ each independently represent an aromatic fused ring group containing a benzene ring surrounded by a broken line as one of the fused rings, $R^5$ and $R^6$ may each independently be substituted with a benzene ring surrounded by a broken line, or may be substituted with a fused ring other than a benzene ring surrounded by a broken line. Similarly, $R^7$ may be substituted with a benzene ring surrounded by a broken line or may be substituted with a fused ring other than a benzene ring surrounded by a broken line.

In General Formula (A), $Ar^{11}$ and $Ar^{12}$ each independently represent an aryl group containing a benzene ring surrounded by a broken line or a heteroaryl group containing a benzene ring surrounded by a broken line. Among them, $Ar^{11}$ and $Ar^{12}$ are each independently preferably an aryl group containing a benzene ring surrounded by a broken line. In the case of the aryl group containing a benzene ring surrounded by a broken line, which is represented by $Ar^{11}$ and $Ar^{12}$, it is preferably an aryl group having 6 to 18 carbon atoms, more preferably an aryl group having 6 to 14 carbon atoms, and particularly preferably an aryl group having 6 to 10 carbon atoms. In the case of the heteroaryl group containing a benzene ring surrounded by a broken line, which is represented by $Ar^{11}$ and $Ar^{12}$, it is preferably a heteroaryl group having 9 to 14 ring members and more preferably a heteroaryl group having 9 or 10 ring members. Examples of the heteroatom constituting the heteroaryl group which may have a substituent represented by $Ar^{11}$ and $Ar^{12}$ include a nitrogen atom, an oxygen atom, and a sulfur atom.

$Ar^{11}$ and $Ar^{12}$ may each independently be an aryl group consisting of only a benzene ring surrounded by a broken line or may be an aromatic fused ring group containing a benzene ring surrounded by a broken line as one of the fused rings.

In General Formula (A), $Ar^{13}$ is an aromatic fused ring group containing a benzene ring surrounded by a broken line as one of the fused rings. The aromatic fused ring group represented by $Ar^{13}$ includes an anthracenyl group and a naphthyl group, among which a naphthyl group is more preferred.

In General Formula (A), $R^{12}$ and $R^{13}$ each independently represent a hydroxyl group, a mercapto group, an amino group, or a group having a polymerizable unsaturated bond. $R^{12}$ and $R^{13}$ are each independently preferably a hydroxyl group or a group having a polymerizable unsaturated bond, and more preferably a hydroxyl group or a polymerizable unsaturated group.

In the case where $Ar^{11}$ and $Ar^{12}$ are each independently an aromatic fused ring group containing a benzene ring surrounded by a broken line as one of the fused rings, $R^{12}$ and $R^{13}$ may each independently be substituted with a benzene ring surrounded by a broken line or may be substituted with a fused ring other than a benzene ring surrounded by a broken line.

In General Formula (A), c to e may each independently be an integer of 0 to 4, preferably an integer of 0 to 3, more preferably an integer of 0 to 2, and still more preferably 0. It is particularly preferred that all of c to e are 0.

(Compound Represented by General Formula (1))

The above compound is preferably a compound represented by General Formula (1). Further, the present invention also relates to a compound described below.

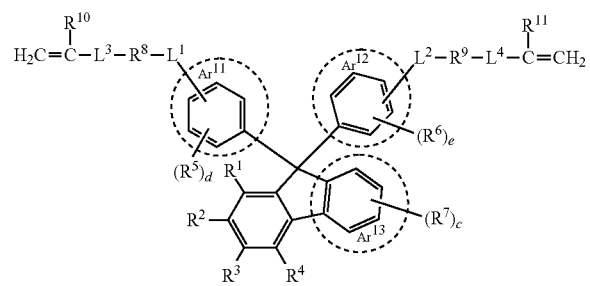

General Formula (1)

In General Formula (1), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring. $R^5$ to $R^7$ each independently represent a substituent. $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings. $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group. c to e each independently represent an integer of 0 to 4. In the case where $Ar^{11}$ and $Ar^{12}$ each independently represent an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line. $R^7$ may be substituted with a benzene ring surrounded by a broken line or may be substituted with a fused ring other than a benzene ring surrounded by a broken line.

A preferred range of $R^1$ to $R^4$ in General Formula (1) is the same as the preferred range of $R^1$ to $R^4$ in General Formula (A).

A preferred range of $R^5$ to $R^7$ in General Formula (1) is the same as the preferred range of $R^5$ to $R^7$ in General Formula (A).

A preferred range of $Ar^{11}$ and $Ar^{12}$ in General Formula (1) is the same as the preferred range of $Ar^{11}$ and $Ar^{12}$ in General Formula (A).

A preferred range of c to e in General Formula (1) is the same as the preferred range of c to e in General Formula (A).

In General Formula (1), $L^1$ and $L^2$ each independently represent a single bond, an oxygen atom, or a sulfur atom. $L^1$ and $L^2$ are each independently preferably an oxygen atom or a sulfur atom and more preferably an oxygen atom.

In General Formula (1), $R^8$ and $R^9$ each independently represent a linking group containing at least one selected from an ether bond, an ester bond, a thioether bond, a thioester bond, an amide bond, a carbonate bond, and an alkylene group, or a single bond. $R^8$ and $R^9$ are each independently preferably a linking group containing at least one selected from an ether bond, an ester bond, a carbonate bond, and an alkylene group, or a single bond, and more preferably a linking group consisting of at least one selected from an ether bond, an ester bond, a carbonate bond, and an alkylene group, or a single bond. In the case where $R^8$ and $R^9$ are a linking group, $R^8$ and $R^9$ each independently preferably include an alkylene group and are more preferably a linking group consisting of an alkylene group. In this case, the number of carbon atoms in the alkylene group is preferably 2 to 8, more preferably 2 to 6, and still more preferably 2 to 4. Incidentally, the alkylene group may have a substituent. By setting the number of carbon atoms in the alkylene group to the above-specified range, the viscosity of the compound represented by General Formula (1) itself can be lowered, and the addition amount of the (meth)acrylate monomer to be described later can also be reduced.

In General Formula (1), $L^3$ and $L^4$ each independently represent a single bond, an ester bond, a thioester bond, or an amide bond. $L^3$ and $L^4$ are each independently preferably an ester bond, a thioester bond, or an amide bond, and more preferably an ester bond. In the case where $L^3$ and $L^4$ represent an ester bond, the ester bond may be any of —C(=O)—O— or —O—C(=O)— from the side of the carbon atom substituted by $R^{10}$ and $R^{11}$, but is preferably —C(=O)—O—.

In the case where $Ar^{11}$ and $Ar^{12}$ are each independently an aromatic fused ring group containing a benzene ring surrounded by a broken line as one of the fused rings, a group having $L^1$ as a linking group, and a group having $L^2$ as a linking group may each independently be substituted with a benzene ring surrounded by a broken line or may be substituted with a fused ring other than a benzene ring surrounded by a broken line.

Here, the group having $L^1$ as a linking group is a group given below.

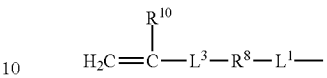

The group having $L^2$ as a linking group is a group given below.

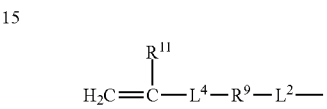

In General Formula (1), $R^{10}$ and $R^{11}$ each independently represent a hydrogen atom or a methyl group, and preferably a hydrogen atom.

The above compound is preferably a compound represented by General Formula (2). Further, the present invention also relates to a compound described below.

General Formula (2)

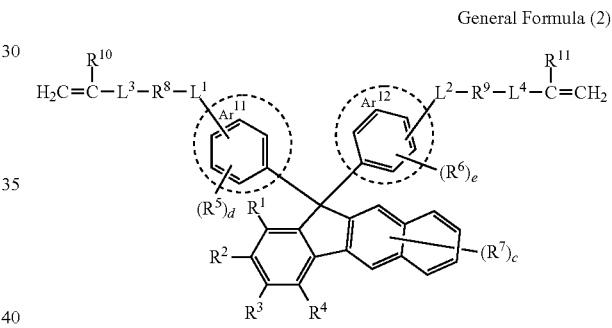

In General Formula (2), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring. $R^5$ to $R^7$ each independently represent a substituent. $Ar^{11}$ and $Ar^{12}$ each independently represent an aryl group containing a benzene ring surrounded by a broken line or a heteroaryl group containing a benzene ring surrounded by a broken line. $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group. c to e each independently represent an integer of 0 to 4. In the case where $Ar^{11}$ and $Ar^{12}$ are each independently an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line.

A preferred range of $R^1$ to $R^4$ in General Formula (2) is the same as the preferred range of $R^1$ to $R^4$ in General Formula (A).

A preferred range of $R^5$ to $R^7$ in General Formula (2) is the same as the preferred range of $R^5$ to $R^7$ in General Formula (A).

A preferred range of $Ar^{11}$ and $Ar^{12}$ in General Formula (2) is the same as the preferred range of $Ar^{11}$ and $Ar^{12}$ in General Formula (A).

A preferred range of $L^1$ and $L^2$ in General Formula (2) is the same as the preferred range of $L^1$ and $L^2$ in General Formula (1).

A preferred range of $R^8$ and $R^9$ in General Formula (2) is the same as the preferred range of $R^8$ and $R^9$ in General Formula (1).

A preferred range of $L^3$ and $L^4$ in General Formula (2) is the same as the preferred range of $L^3$ and $L^4$ in General Formula (1).

A preferred range of $R^{10}$ and $R^{11}$ in General Formula (2) is the same as the preferred range of $R^{10}$ and $R^{11}$ in General Formula (1).

A preferred range of c to e in General Formula (2) is the same as the preferred range of c to e in General Formula (A).

Hereinafter, specific examples of the compound represented by General Formula (A) which is preferably used in the present invention are shown, but the present invention is not limited to the following compounds.

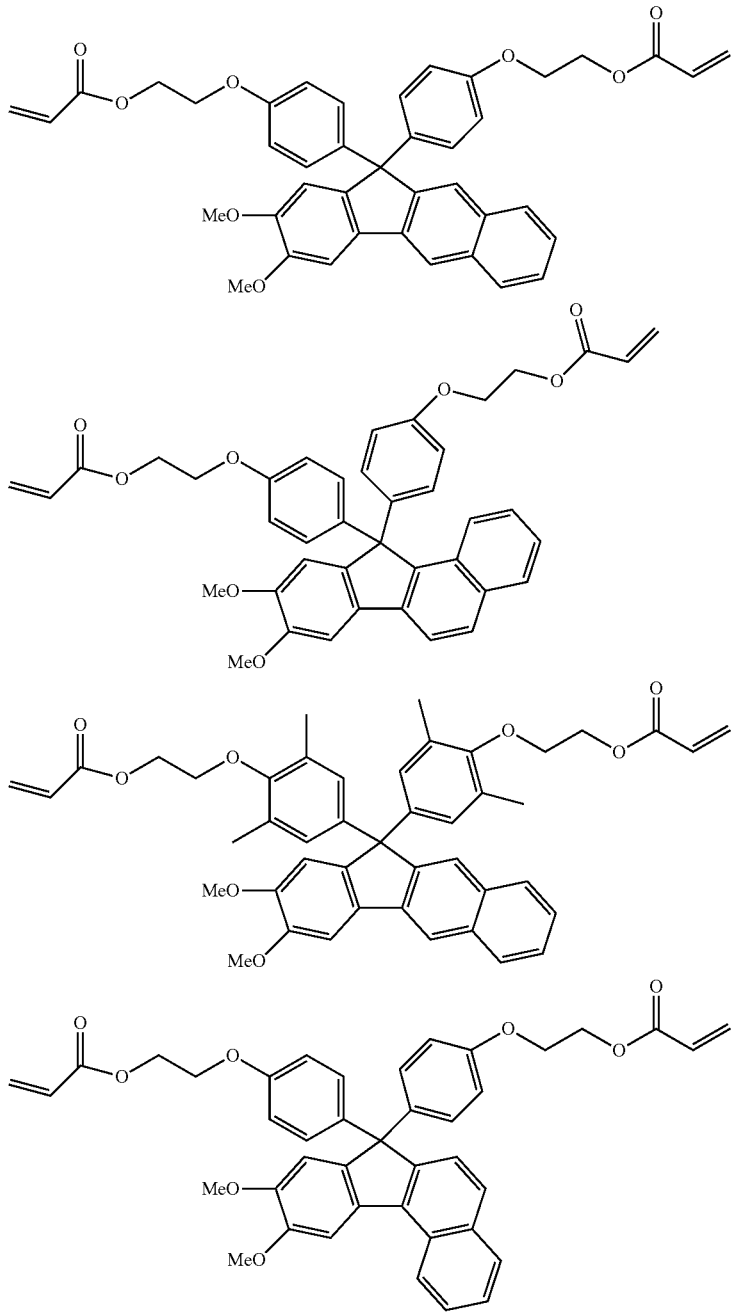

-continued
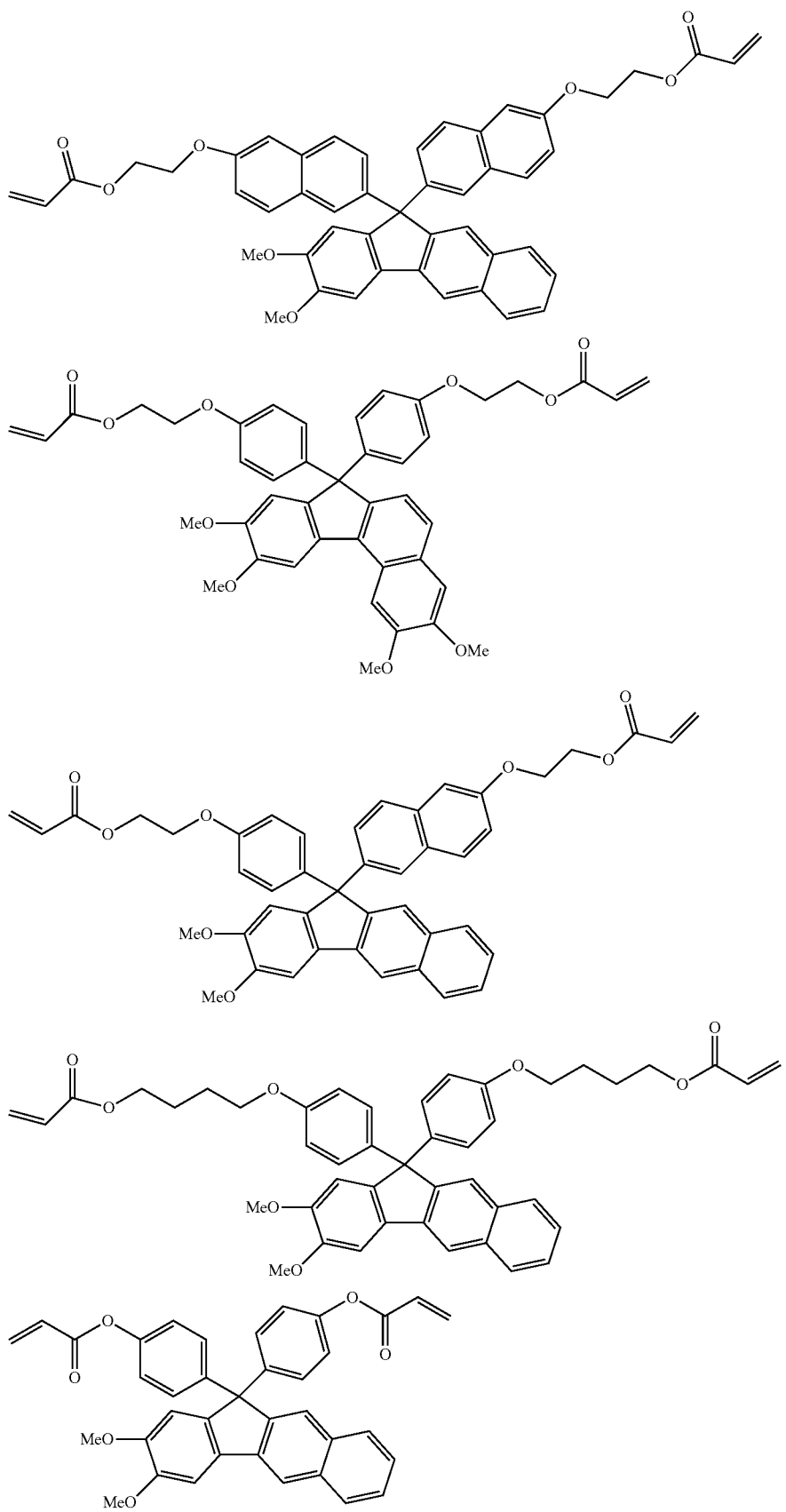

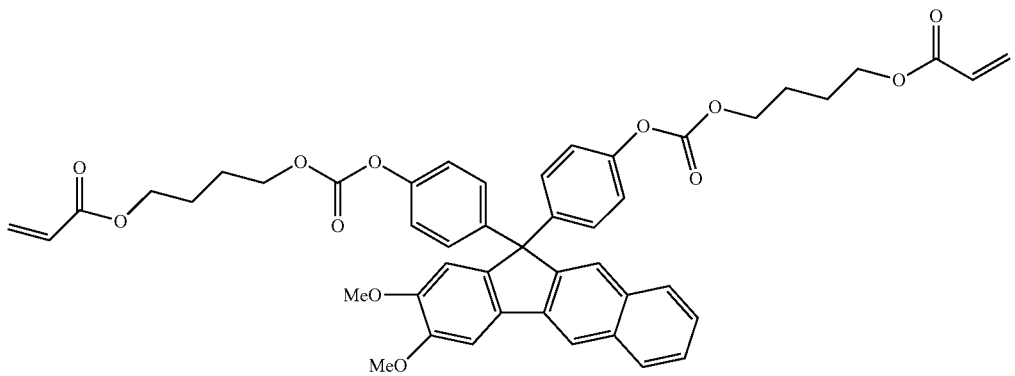
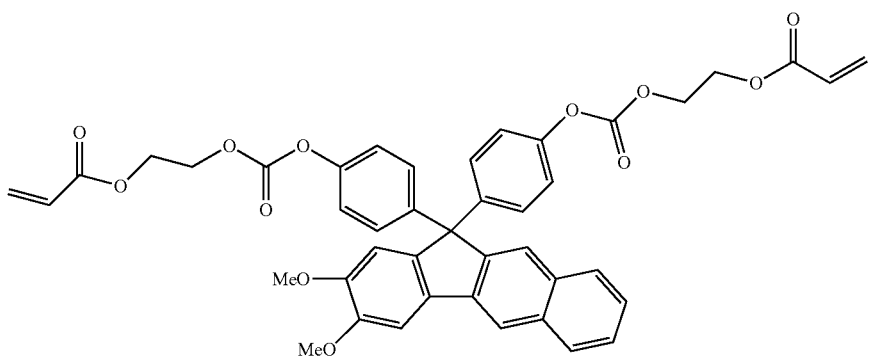
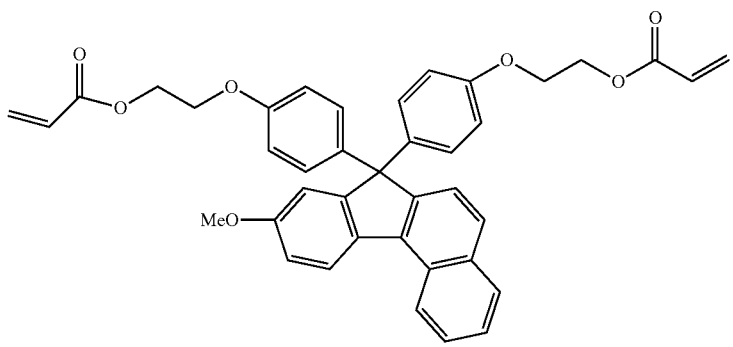
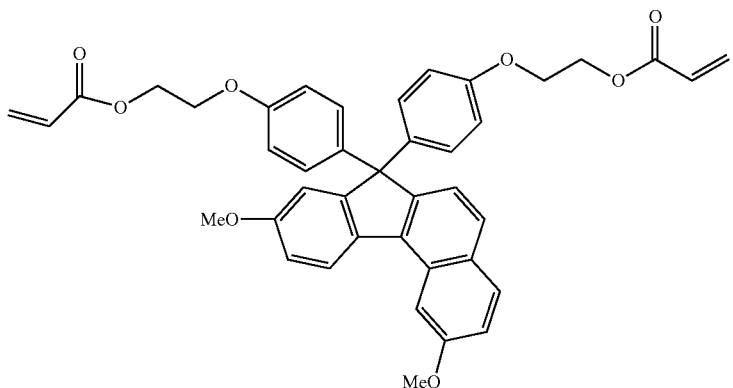

-continued
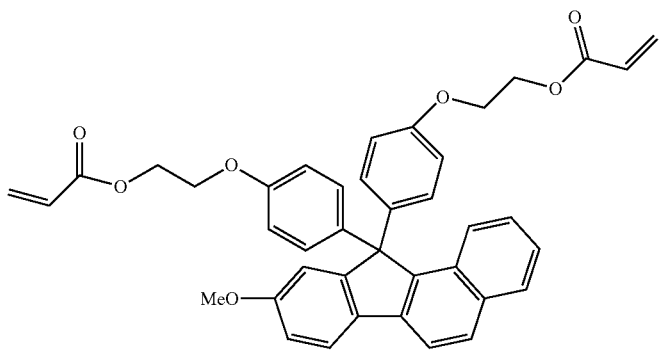
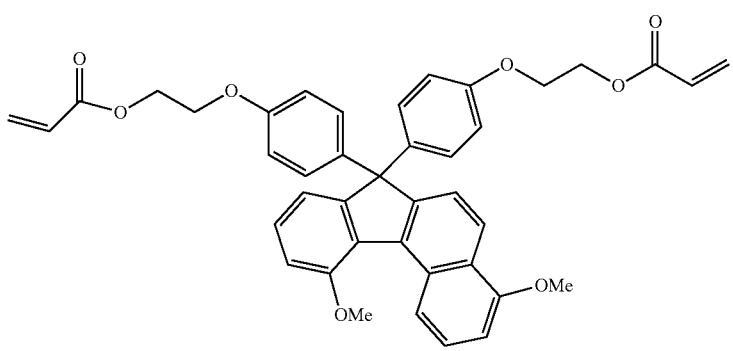
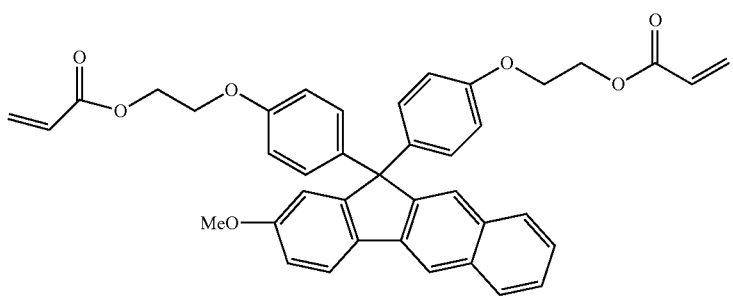
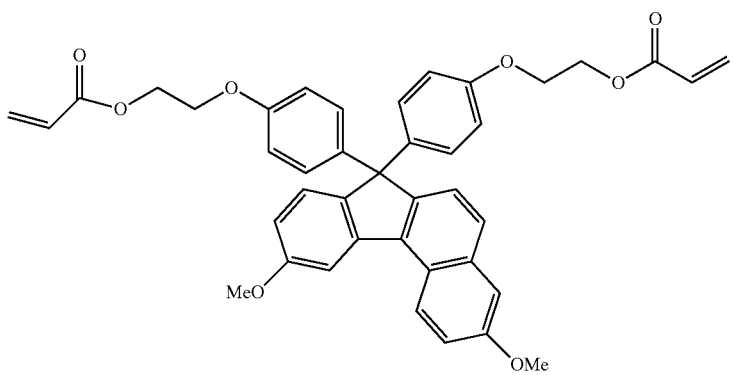

-continued
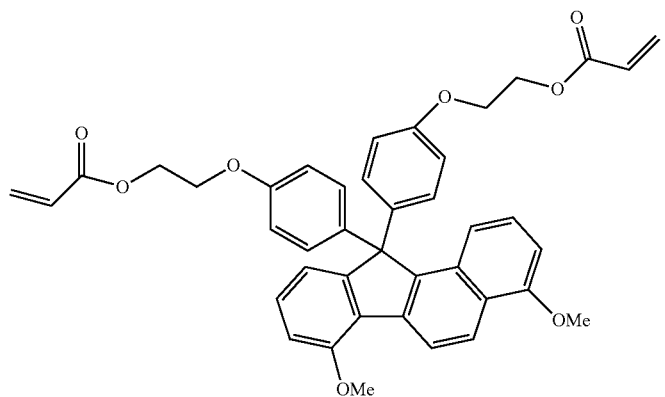
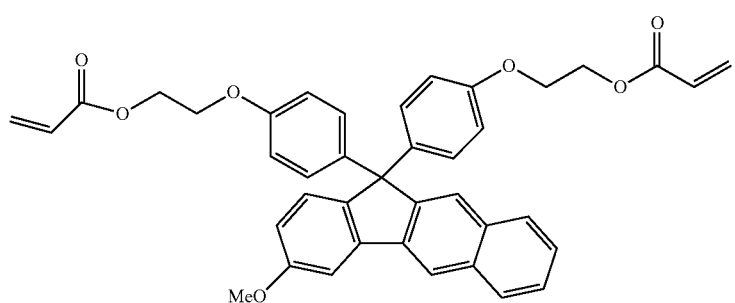
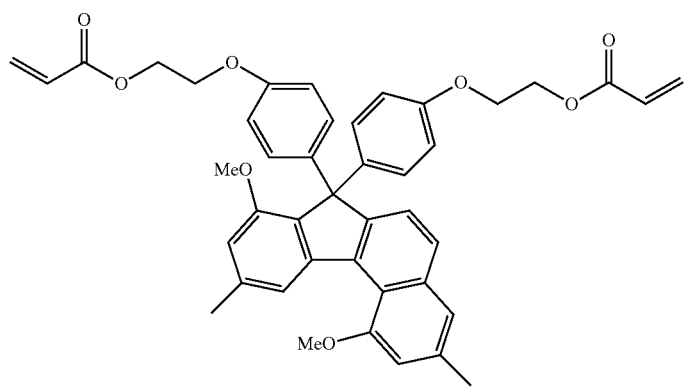
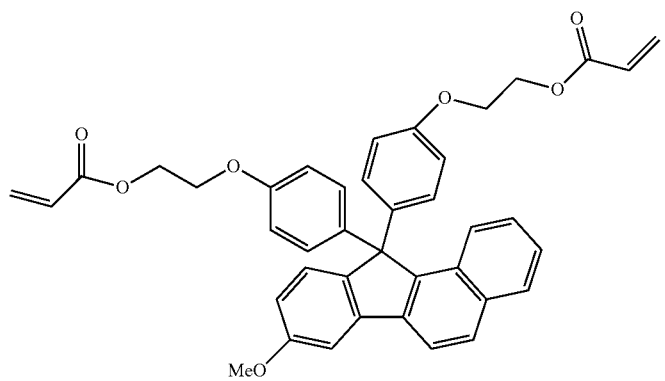

-continued
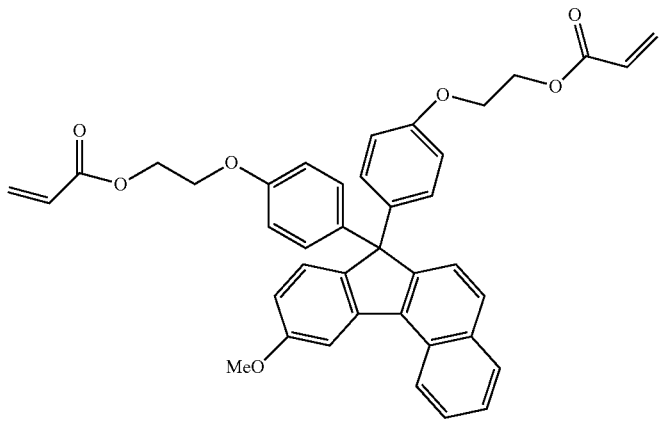
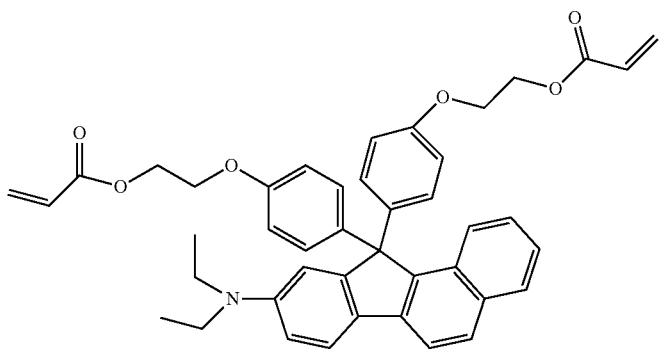
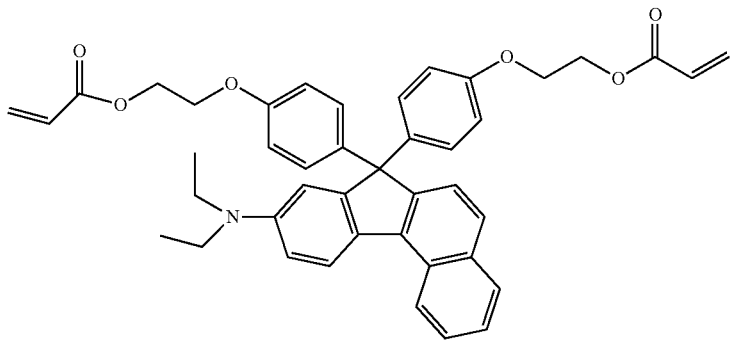
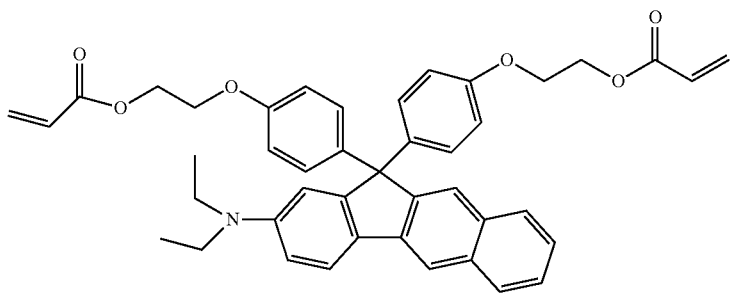
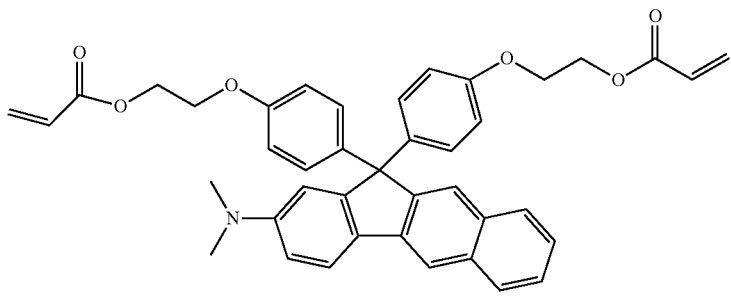
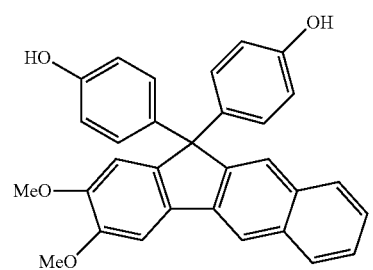

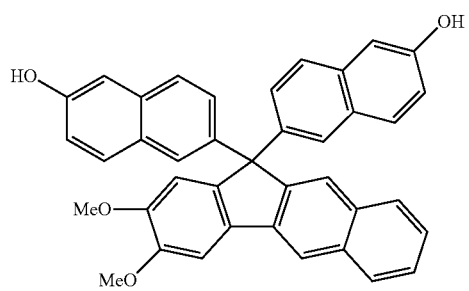
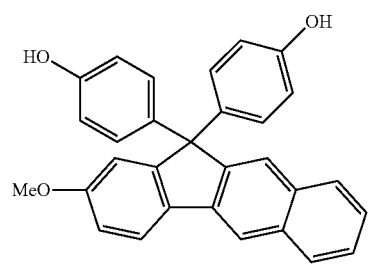
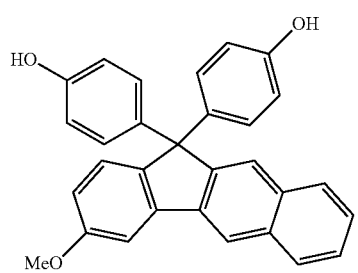 [SMILES: COc1ccc2c(c1)-c1cc3ccccc3cc1C2(c1ccc(O)cc1)c1ccc(O)cc1]
Among them, the compound represented by General Formula (A) is preferably any one of Compounds 2-1 to 2-9 given below.
Compound 2-1
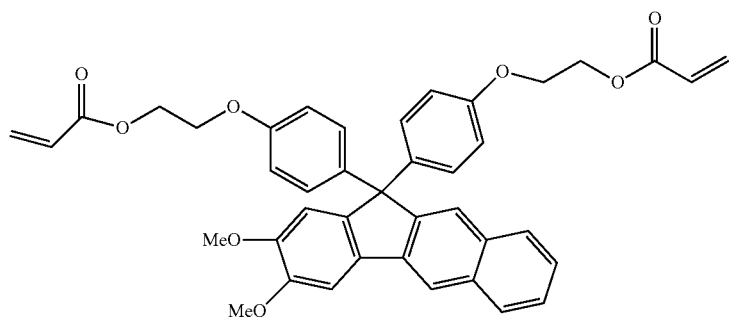
Compound 2-2
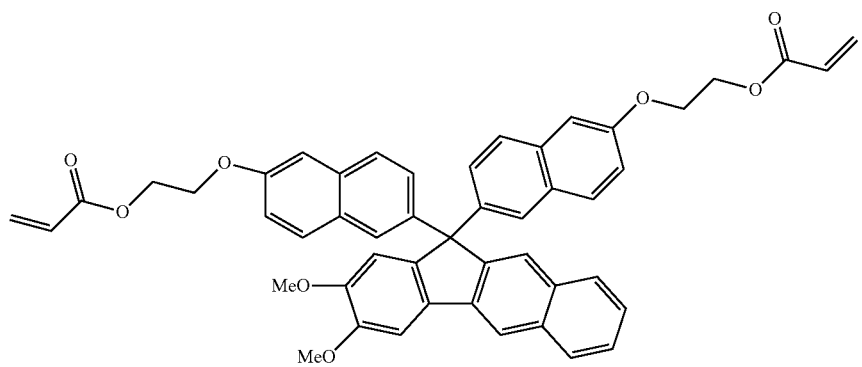

Compound 2-3
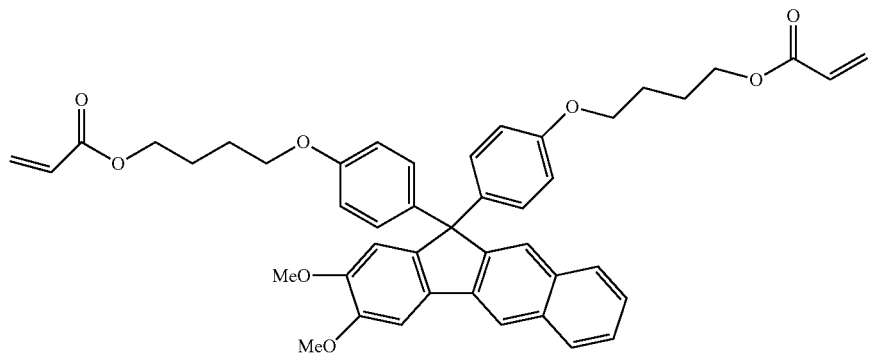
Compound 2-4
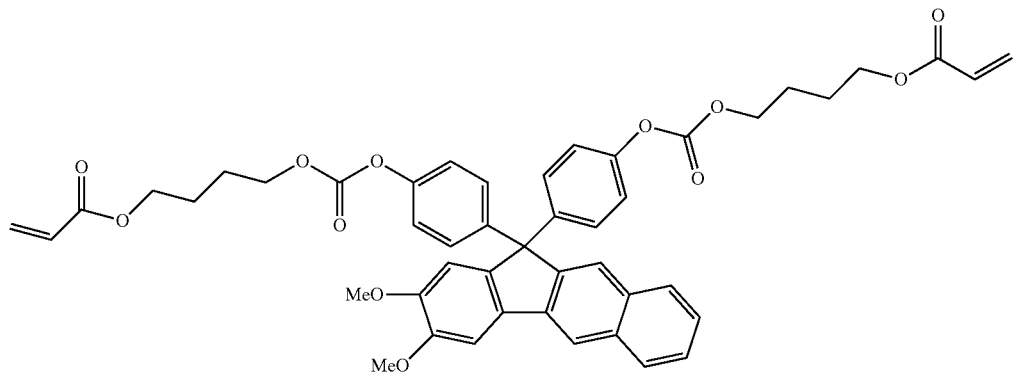
Compound 2-5 Compound 2-6
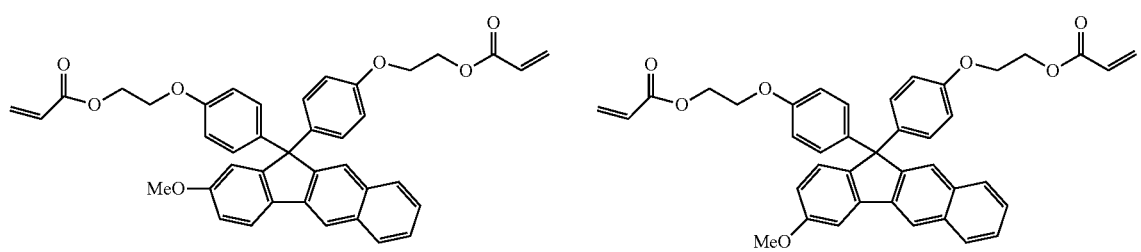
Compound 2-7 Compound 2-8
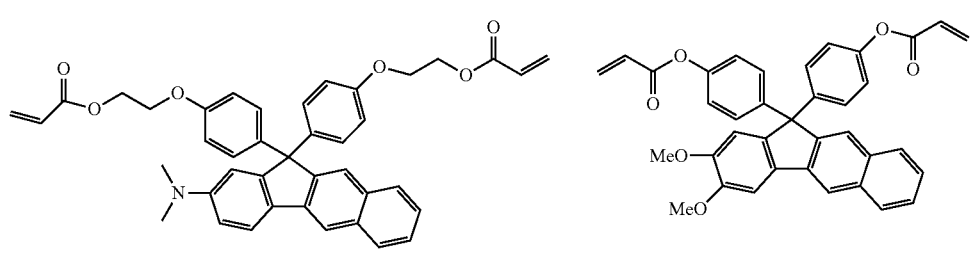
Compound 2-9
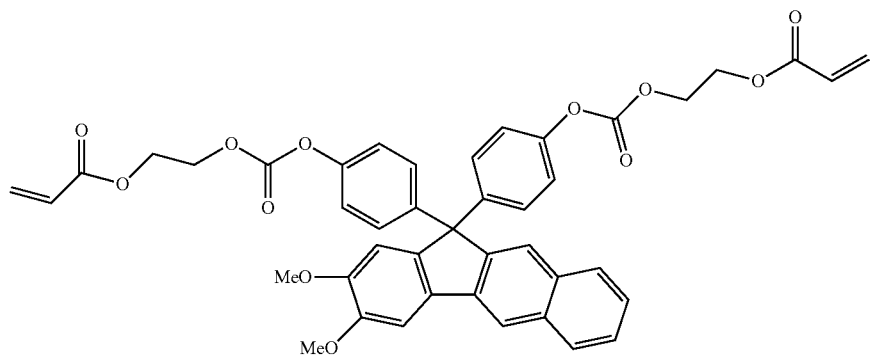

The molecular weight of the compound represented by General Formula (A) is preferably 400 to 1,000, more preferably 500 to 900, and particularly preferably 550 to 800.

The method of obtaining these compounds represented by General Formula (A) is not particularly limited, and the compounds may be commercially available or may be produced by synthesis. In the case of production by synthesis, the method for producing the compound represented by General Formula (A) is not particularly limited and the compound can be synthesized by known methods and methods described in the Examples.

The content of the compound represented by General Formula (A) in the curable composition is preferably 20 to 94 mass %, more preferably 40 to 85 mass %, and still more preferably 50 to 85 mass %.

((Meth)Acrylate Monomer)

The curable composition of the present invention includes a (meth)acrylate monomer having a viscosity at 25° C. of less than 2,000 mPa·s. The viscosity at 25° C. of the (meth)acrylate monomer is preferably less than 1,500 mPa·s, more preferably less than 1,000 mPa·s, still more preferably less than 500 mPa·s, and particularly preferably less than 200 mPa·s. The viscosity at 25° C. of the (meth)acrylate monomer can be measured using a rheometer (RS 600, manufactured by HAAKE GmbH) under conditions of 25° C. and a shear rate of 10 s$^{-1}$.

The (meth)acrylate monomer may be a monofunctional (meth)acrylate monomer having one (meth)acryloyl group in the molecule, or a polyfunctional (meth)acrylate monomer having two or more (meth)acryloyl groups in the molecule. Among them, a monofunctional (meth)acrylate monomer is preferably used.

Examples of the monofunctional (meth)acrylate monomer used in the present invention include adamantyl (meth)acrylates such as 1-adamantyl (meth)acrylate, norbornyl (meth)acrylates such as isobornyl (meth)acrylate, tricyclodecane (meth)acrylates such as tricyclo[5,2,1,0$^{2,6}$]deca-8-yl acrylate, 2-ethyl-2-butylpropanediol (meth)acrylate, 2-ethylhexyl (meth)acrylate, 2-ethylhexylcarbitol (meth)acrylate, 2-hydroxybutyl (meth)acrylate, 2-hydroxyethyl (meth)acrylate, 2-hydroxypropyl (meth)acrylate, 2-methoxyethyl (meth)acrylate, 3-methoxybutyl (meth)acrylate, 4-hydroxybutyl (meth)acrylate, benzyl (meth)acrylate, butanediol mono(meth)acrylate, butoxyethyl (meth)acrylate, butyl (meth)acrylate, cetyl (meth)acrylate, ethylene oxide (EO)-modified cresol (meth)acrylate, dipropylene glycol (meth)acrylate, ethoxylated phenyl (meth)acrylate, ethyl (meth)acrylate, isoamyl (meth)acrylate, isobutyl (meth)acrylate, isooctyl (meth)acrylate, cyclohexyl (meth)acrylate, dicyclopentanyl (meth)acrylate, dicyclopentanyloxy ethyl (meth)acrylate, isomyristyl (meth)acrylate, lauryl (meth)acrylate, methoxydipropylene glycol (meth)acrylate, methoxytripropylene glycol (meth)acrylate, methoxypolyethylene glycol (meth)acrylate, methoxytriethylene glycol (meth)acrylate, methyl (meth)acrylate, neopentyl glycol benzoate (meth)acrylate, nonylphenoxypolyethylene glycol (meth)acrylate, nonylphenoxypolypropylene glycol (meth)acrylate, octyl (meth)acrylate, paracumylphenoxyethylene glycol (meth)acrylate, epichlorohydrin (ECH)-modified phenoxy(meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, stearyl (meth)acrylate, EO-modified succinic acid (meth)acrylate, tert-butyl (meth)acrylate, tribromophenyl (meth)acrylate, EO-modified tribromophenyl (meth)acrylate, and tridodecyl (meth)acrylate.

The (meth)acrylate monomer is preferably a (meth)acrylate monomer containing an aryl group or a heteroaryl group. Among them, the (meth)acrylate monomer is more preferably a monofunctional (meth)acrylate monomer containing an aryl group or a heteroaryl group. Use of a (meth)acrylate monomer containing an aryl group or a heteroaryl group as the (meth)acrylate monomer can lead to an effective reduction of an Abbe's number of a cured product. Further, use of a (meth)acrylate monomer containing an aryl group or a heteroaryl group readily brings about uniform mixing of the (meth)acrylate monomer in the curable composition, so the transparency and durability of the cured product can be more effectively enhanced.

Examples of the (meth)acrylate monomer containing an aryl group or a heteroaryl group include benzyl (meth)acrylate, EO-modified cresol (meth)acrylate, ethoxylated phenyl (meth)acrylate, nonylphenoxypolyethylene glycol (meth)acrylate, nonylphenoxypolypropylene glycol (meth)acrylate, paracumylphenoxyethylene glycol (meth)acrylate, ECH-modified phenoxy(meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, tribromophenyl (meth)acrylate, EO-modified tribromophenyl (meth)acrylate, O-phenylphenol (meth)acrylate, and O-phenylphenol EO-modified (meth)acrylate. Among them, benzyl (meth)acrylate, phenoxyethyl (meth)acrylate, O-phenylphenol (meth)acrylate, and O-phenylphenol EO-modified (meth)acrylate are more preferable, benzyl (meth)acrylate and phenoxyethyl (meth)acrylate are particularly preferable, and benzyl acrylate and phenoxyethyl acrylate are particularly more preferable.

The (meth)acrylate monomer may be an alicyclic (meth)acrylate monomer. The alicyclic (meth)acrylate monomer may be one in which one (meth)acryloyl group is bonded to an aliphatic ring directly or through a divalent linking group, or one in which two or more (meth)acryloyl groups are bonded to an aliphatic ring directly or through a divalent linking group. Among them, a monofunctional (meth)acrylate monomer in which one (meth)acryloyl group is directly bonded to an aliphatic ring is preferably used.

The aliphatic ring may have a monocyclic structure or a polycyclic structure in which two or more aliphatic rings are linked or fused, and may contain a bridged ring hydrocarbon. In addition, the aliphatic ring may consist of only a carbon atom and a hydrogen atom, or may contain a heteroatom in addition to a carbon atom and a hydrogen atom. The number of carbon atoms in the aliphatic ring is not particularly limited, but it is preferably 6 to 20, more preferably 7 to 15, and still more preferably 7 to 10. Specifically, the aliphatic ring is preferably tricyclodecane, adamantane, norbornane, cyclohexane, or norbornene, more preferably tricyclodecane, adamantane, or norbornane, and still more preferably tricyclodecane.

As the (meth)acrylate monomer which can be preferably used in the present invention, for example, the following compounds can be listed.

Monomer 1

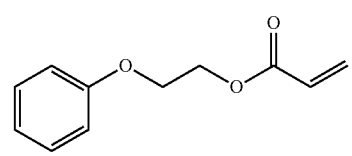

Monomer 2

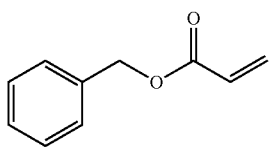

Monomer 3

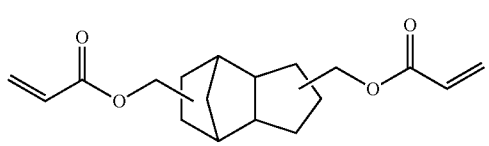

Monomer 4

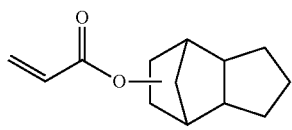

The method of obtaining the (meth)acrylate monomer is not particularly limited, and the compound may be commercially available or may be produced by synthesis. In the case of commercially obtaining the compound, for example, VISCOAT #192 PEA (Monomer 1) (manufactured by Osaka Organic Chemical Industry Ltd.), VISCOAT #160 BZA (Monomer 2) (manufactured by Osaka Organic Chemical Industry Ltd.), VISCOAT #160 BZA (Monomer 2) (manufactured by Osaka Organic Chemical Industry Ltd.), A-DCP (Monomer 3) (manufactured by Shin-Nakamura Chemical Co., Ltd.), or FA-513AS (Monomer 4) (manufactured by Hitachi Chemical Co., Ltd.) may be preferably used. The viscosity of Monomer 1 at 25° C. and a shear rate of 10 $s^{-1}$ is 9 mPa·s, the viscosity of Monomer 2 at 25° C. and a shear rate of 10 $s^{-1}$ is 8 mPa·s, the viscosity of Monomer 3 at 25° C. and a shear rate of 10 $s^{-1}$ is 120 mPa·s, and the viscosity of Monomer 4 at 25° C. and a shear rate of 10 $s^{-1}$ is 12 mPa·s.

The content of the (meth)acrylate monomer having a viscosity at 25° C. of less than 2,000 mPa·s in the curable composition is preferably 5 to 80 mass %, more preferably 5 to 50 mass %, and still more preferably 5 to 40 mass %.

(Non-Conjugated Vinylidene Group-Containing Compound)

The curable composition of the present invention preferably further contains a non-conjugated vinylidene group-containing compound represented by General Formula (3), and more preferably a non-conjugated vinylidene group-containing compound represented by General Formula (4).

General Formula (3)

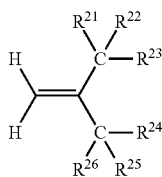

In General Formula (3), $R^{21}$ to $R^{26}$ each independently represent a substituent, at least one of $R^{21}$, $R^{22}$, $R^{23}$, $R^{24}$, $R^{25}$, or $R^{26}$ forms a ring, or at least two of $R^{21}$, $R^{22}$, $R^{23}$, $R^{24}$, $R^{25}$, or $R^{26}$ are bonded to each other to form a ring. However, the non-conjugated vinylidene group-containing compound represented by General Formula (3) does not contain a (meth)acryloyl group.

According to the present invention, the viscosity of the semi-cured product after photo- or thermal polymerization can be controlled to be within a specific range and the heat resistance and the yield of the cured product obtained when the semi-cured product is subjected to the thermal polymerization in the method for producing a cured product described below can be improved, by using the curable composition containing such a non-conjugated vinylidene group-containing compound represented by General Formula (3).

The substituent represented by $R^{21}$ to $R^{26}$ in General Formula (3) is not particularly limited and examples thereof include a hydrogen atom, a halogen atom, a halogenated alkyl group, an alkyl group, an alkenyl group, an acyl group, a hydroxyl group, a hydroxyalkyl group, an aromatic ring group, a heteroaromatic ring group, and an alicyclic group. Among them, $R^{21}$ to $R^{26}$ are preferably a hydrogen atom, an alkyl group, or an alkenyl group, and more preferably a hydrogen atom, an alkyl group having 1 to 5 carbon atoms, or an alkenyl group having 2 to 5 carbon atoms.

The ring formed by $R^{21}$ to $R^{26}$ may be an aromatic ring or a heteroaromatic ring, and may also be a non-aromatic ring. Above all, the ring to be formed by $R^{21}$ to $R^{26}$ is preferably a non-aromatic ring and more preferably a non-aromatic hydrocarbon ring. The ring to be formed by $R^{21}$ to $R^{26}$ may further have a substituent, and for example, the substituent is preferably an alkyl group having 1 to 5 carbon atoms and more preferably a methyl group, an ethyl group, an n-propyl group, or an isopropyl group. In the case where the ring to be formed by $R^{21}$ to $R^{26}$ has additional substituents, the substituents may be bonded to each other to form a fused ring.

The non-conjugated vinylidene group-containing compound represented by General Formula (3) may have one ring or multiple rings formed by $R^{21}$ to $R^{26}$ therein. In the case where the compound has multiple rings formed by $R^{21}$ to $R^{26}$, the rings may be multiple rings independent of each other, or those independent multiple rings may be condensed to form a fused ring, or in the case where one ring has additional substituents, the substituents may be bonded to each other to form a fused ring. Above all, the ring to be formed by $R^{21}$ to $R^{26}$ is more preferably a fused ring formed through condensation of multiple rings; and in the case where one ring has additional substituents, particularly preferably, the substituents are bonded to each other to form a fused ring. In this description, an embodiment where two rings form a spiro-condensation like the specific compounds mentioned below is also within the scope of the concept of the fused ring here. Of the carbon atom to which $R^{21}$ and $R^{22}$ are bonded and the carbon atom to which $R^{25}$ and $R^{26}$ are bonded, one carbon atom is preferably an asymmetric carbon atom.

The non-conjugated vinylidene group-containing compound represented by General Formula (3) preferably contains a fused ring formed through condensation of 2 to 5 rings and more preferably a fused ring formed through condensation of 2 or 3 rings. In addition, the number of the ring-constituting atoms of each ring constituting the fused ring is preferably 3 to 10, more preferably 3 to 9, and particularly preferably 4 to 9.

Of $R^{21}$ to $R^{26}$, (A) at least one forms a ring, or (B) at least two are bonded to each other to form a ring. Of $R^{21}$ to $R^{26}$ in the non-conjugated vinylidene group-containing compound, case (B) is preferred where at least two are bonded to each other to form a ring. In this case, it is preferred that the non-conjugated vinylidene group-containing compound is represented by General Formula (4).

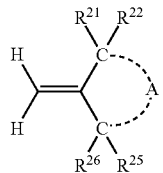

General Formula (4)

In General Formula (4), $R^{21}$, $R^{22}$, $R^{25}$, and $R^{26}$ each independently represent a substituent, and A represents an atomic group necessary for forming a cyclic structure.

In General Formula (4), the preferred range of the substituent represented by $R^{21}$, $R^{22}$, $R^{25}$, and $R^{26}$ is the same as that of $R^{21}$ to $R^{26}$ in General Formula (3). $R^{21}$, $R^{22}$, $R^{25}$, and $R^{26}$ may be bonded to one another to form a ring, and the ring may additionally have a substituent.

Preferably, of the pair of $R^{21}$ and $R^{22}$ or the pair of $R^{25}$ and $R^{26}$, at least one of the two substituents in any one pair alone is a hydrogen atom, and more preferably, both the two substituents in any one pair alone are hydrogen atoms.

Also preferably, $R^{21}$ and $R^{22}$ are each independently a hydrogen atom or a hydrocarbon group having 1 to 5 carbon atoms, and the hydrocarbon group having 1 to 5 carbon atoms does not form a ring. Of $R^{21}$ and $R^{22}$, preferably, one alone is a hydrogen atom or a hydrocarbon group having 1 to 5 carbon atoms, and the hydrocarbon group having 1 to 5 carbon atoms does not form a ring.

In General Formula (4), A represents an atomic group necessary for forming a cyclic structure, and the cyclic structure is not particularly limited and may be any known cyclic structure. Examples of the cyclic structure include an alicyclic ring (non-aromatic hydrocarbon ring), an aromatic ring, a heterocyclic ring, and a lactone ring containing —CO—. Of those, A is preferably an atomic group necessary for forming an alicyclic ring having 4 to 10 carbon atoms including the carbon atoms bonded to A in General Formula (4) and the carbon atom constituting the non-conjugated vinylidene group, and particularly preferably an atomic group necessary for forming an alicyclic ring having 5 to 9 carbon atoms including the carbon atoms bonding to A in General Formula (4) and the carbon atom constituting the non-conjugated vinylidene group. The alicyclic ring may have an additional substituent, and the preferred range of the substituent is the same as that of the additional substituent that the ring to be formed by $R^{21}$, $R^{22}$, $R^{25}$, and $R^{26}$ may have. A may be an unsaturated alicyclic ring or a saturated alicyclic ring, but it is preferred that at least one unsaturated bond is contained in the entire non-conjugated vinylidene group-containing compound represented by General Formula (4). A may further form a fused ring along with the substituent represented by $R^{21}$, $R^{22}$, $R^{25}$, and $R^{26}$.

According to the present invention, in General Formula (4), it is particularly preferred that $R^{21}$, $R^{22}$, $R^{25}$, and $R^{26}$ each independently represent a substituent consisting of only hydrogen atoms and carbon atoms, and A represents an alicyclic (non-aromatic hydrocarbon) structure.

In the present invention, the non-conjugated vinylidene group-containing compound represented by General Formula (3) or (4) preferably has an additional alkenyl group in addition to the vinylidene group (non-conjugated vinylidene group). The position of the vinylidene group other than the non-conjugated vinylidene group contained in the non-conjugated vinylidene group-containing compound represented by General Formula (3) or (4) is not particularly limited. Among them, the non-conjugated vinylidene group-containing compound represented by General Formula (3) or (4) preferably has a vinylidene group other than the non-conjugated vinylidene group on the ring formed by $R^{21}$, $R^{22}$, $R^{25}$, and $R^{26}$. That is, the ring formed by $R^{21}$, $R^{22}$, $R^{25}$, and $R^{26}$ preferably contains at least one unsaturated hydrocarbon ring, and more particularly preferably at least one unsaturated hydrocarbon ring that has only one double bond.

The molecular weight of the non-conjugated vinylidene group-containing compound used in the present invention is preferably 100 to 400, more preferably 120 to 350, and particularly preferably 130 to 300.

The method of obtaining the non-conjugated vinylidene group-containing compound is not particularly limited, and the compound may be commercially available or may be produced by synthesis. In the case of commercially obtaining the compound, for example, β-caryophyllene of the compound (B-5) (manufactured by Inoue Perfumery Co., Ltd.) may be preferably used.

In the case of producing the compound by synthesis, the method for producing the non-conjugated vinylidene group-containing compound represented by General Formula (3) or (4) is not particularly limited and the compound may be produced by any known method. For example, in the case of synthesizing β-caryophyllene which can be preferably used in the present invention, the compound may be produced according to the method described in J. Am. Chem. Soc. 85, 362 (1964), Tetrahedron Lette., 24, 1885 (1983), or the like.

The content of the non-conjugated vinylidene group-containing compound in the curable composition is preferably 0.5 to 30 mass %, more preferably 1 to 25 mass %, and still more preferably 2 to 20 mass %.

<Photoradical Polymerization Initiator>

The curable composition of the present invention contains at least one selected from a photoradical polymerization initiator and a thermal radical polymerization initiator. The photoradical polymerization initiator is not particularly limited and may be any known photoradical polymerization initiator.

Specifically, the following compounds can be used as the photoradical polymerization initiator. Examples of the photoradical polymerization initiator include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)butanone-1,2,4,6-trimethylbenzoyl-diphenyl-phosphine oxide, and bis(2,4,6-trimethylbenzoyl)-phenylphosphine oxide.

Of the above, in the present invention, BASF's Irgacure 184 (1-hydroxycyclohexyl phenyl ketone), 1-[4-(2-hydroxyethoxy)-phenyl]-2-hydroxy-2-methyl-1-propan-1-one, 2-methyl-1-(4-methylthiophenyl)-2-morpholinopropan-1-one, or 2,2-dimethoxy-1,2-diphenylethan-1-one may be preferably used as the photoradical polymerization initiator.

The content of the photoradical polymerization initiator in the curable composition is preferably 0.01 to 5.0 mass %, more preferably 0.05 to 1.0 mass %, and still more preferably 0.05 to 0.5 mass %.

<Thermal Radical Polymerization Initiator>

The curable composition of the present invention preferably contains a thermal radical polymerization initiator. By adding a thermal radical polymerization initiator to the curable composition in advance, it is possible to mold a cured product having high heat resistance through thermal polymerization of a semi-cured product obtained by semi-curing the curable composition.

Specifically, the following compounds can be used as the thermal radical polymerization initiator. Examples of the thermal radical polymerization initiator include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, and 2,3-dimethyl-2,3-diphenylbutane.

Above all, in the present invention, it is preferable to use a hydroperoxide-based thermal radical polymerization initiator having a hydroperoxide group in the molecule as the thermal radical polymerization initiator, and it is more preferable to use at least one hydroperoxide-based thermal radical polymerization initiator having a hydroperoxide group in the molecule and at least one non-hydroperoxide-based thermal radical polymerization initiator having no hydroperoxide group in the molecule.

In the present invention, PERBUTYL O (t-butylperoxy-2-ethylhexanoate, manufactured by NOF Corporation) can be preferably used as the non-hydroperoxide-based thermal radical polymerization initiator, and PERCUMYL H-80 (cumene hydroperoxide, manufactured by NOF Corporation) can be preferably used as the hydroperoxide-based thermal radical polymerization initiator.

The reason why use of the hydroperoxide-based thermal radical polymerization initiator having a hydroperoxide group in the molecule is preferred as the thermal radical polymerization initiator is because the hydroperoxide-based thermal radical polymerization initiator has an effect of promoting a chain transfer during polymerization of a non-conjugated vinylidene group-containing compound monomer by which the three-dimensional structure of the resulting polymer can be more favorably controlled and the semi-cured product can be given good deformability. In a case where such a hydroperoxide-based thermal radical polymerization initiator is used, the temperature at which thermal radical polymerization is initiated is generally high, and therefore in such a case, it is more preferable that the hydroperoxide-based thermal radical polymerization initiator is used along with a non-hydroperoxide-based thermal radical polymerization initiator having a low thermal polymerization initiation temperature.

The content of the thermal radical polymerization initiator in the curable composition is preferably 0.01 to 10 mass %, more preferably 0.05 to 5.0 mass %, and still more preferably 0.05 to 2.0 mass %.

The curable composition preferably contains both a photoradical polymerization initiator and a thermal radical polymerization initiator described above, and in this case, the total content of a photoradical polymerization initiator and a thermal radical polymerization initiator is preferably 0.01 to 10 mass %, more preferably 0.05 to 5.0 mass %, and still more preferably 0.05 to 3.0 mass %.

(Other Additives)

According to the present invention, the curable composition may contain additives such as a polymer, another monomer, a dispersant, a plasticizer, a thermal stabilizer, and a mold release agent within the range not departing from the scope of the present invention.

(Method for Producing Semi-Cured Product)

The semi-cured product can be produced by semi-curing the curable composition of the present invention. The method for producing a semi-cured product includes a step of semi-curing the curable composition of the present invention. The step of semi-curing may be a step of photoirradiation or heating. In particular, the step of semi-curing preferably includes a step of photoirradiating the curable composition of the present invention.

In the step of semi-curing, the curable composition of the present invention is preferably subjected to at least one of photoirradiation or heating to form a semi-cured product having a complex viscosity of $10^5$ to $10^8$ mPa·s at 25° C. and at a frequency of 10 Hz, and the curable composition of the present invention is more preferably subjected to photoirradiation to form a semi-cured product having a complex viscosity of 10 to 10 mPa·s at 25° C. and at a frequency of 10 Hz.

As used herein, the term "semi-cured product" refers to a product obtained by polymerizing a curable composition, which is not completely solid and has fluidity to some extent. For example, a polymer of a curable composition in such a state that its complex viscosity at 25° C. and at a frequency of 10 Hz is $10^5$ to $10^8$ mPa·s is a semi-cured product. That is, those of which the upper limit value of the complex viscosity at 25° C. and at a frequency of 10 Hz is up to $1.0 \times 10^9$ mPa·s are considered to fall within a range of semi-cured products. On the other hand, the term "cured product" refers to a product produced by polymerizing a curable composition and is in a state of being completely solid.

Hereinafter, the method for producing a semi-cured product and the method for producing a cured product will be specifically described. The method for producing a cured product includes the method for producing a semi-cured product, and therefore preferred embodiments of the production method common to both the two are described in the section of Method for producing semi-cured product.

<Semi-Curing Step>

The method for producing a semi-cured product preferably includes a step of photoirradiating and/or heating the curable composition to give a semi-cured product having a complex viscosity of $10^5$ to $10^8$ mPa·s at 25° C. and at a frequency of 10 Hz.

In the method for producing a semi-cured product, the curable composition may be directly placed in a mold to be used in thermal polymerization, before photoirradiation and/or heating of the composition, or alternatively, the curable composition may be placed in a mold different from the mold for thermal polymerization to give a semi-cured product, and then transferred to the mold to be used in thermal polymerization.

In the case where a mold different from the mold for thermal polymerization is used, preferred is the use of a so-called mold for preforming. The mold for preforming may be formed of metal, or may be formed of glass or resin. In consideration of using the mold repeatedly in a mass-production line, the mold for preforming is preferably formed of metal or glass. In the case where the semi-cured product is used for lenses, it is preferred that at least one side of the mold for preforming has a shape that is the same as/or similar to the shape of the mold for thermal polymerization, and it is more preferred that both sides of the mold for preforming have a shape that is the same as/or similar to the shape of the mold for thermal polymerization.

(Conditions for Photoirradiation)

The photoirradiation in the method for producing a semi-cured product is carried out so that the complex viscosity of the semi-cured product at 25° C. and at a frequency of 10 Hz after photoirradiation is preferably $10^5$ to $10^8$ mPa·s, more preferably $10^5$ to $10^{7.5}$ mPa·s, and particularly preferably $10^{5.5}$ to $10^{7.5}$ mPa·s.

The light used in the photoirradiation is preferably ultraviolet light or visible light and more preferably ultraviolet light. For example, a metal halide lamp, a low pressure mercury lamp, a high pressure mercury lamp, an ultrahigh pressure mercury lamp, a germicidal lamp, a xenon lamp, or a light emitting diode (LED) light source lamp is preferably used. The atmosphere during photoirradiation is preferably in the air or after purging with an inert gas and is more preferably an atmosphere purged with nitrogen until an oxygen concentration becomes 1% or less.

(Conditions for Semi-Curing by Heating)

In the case of providing a semi-curing step by heating in the method for producing a semi-cured product, the semi-curing by heating is carried out so that the complex viscosity of the semi-cured product at 25° C. and at a frequency of 10 Hz after heating is preferably $10^5$ to $10^8$ mPa·s, more preferably $10^5$ to $10^{7.5}$ mPa·s, and particularly preferably $10^{5.5}$ to $10^{7.5}$ mPa·s.

(Semi-Cured Product)

The present invention may relate to a semi-cured product produced by the above-described method. Such a semi-cured product may be preferably used for a method for producing a cured product to be described later. Here, the preferred range of the complex viscosity of the semi-cured product is the same as the preferred range of the complex viscosity of the semi-cured product in the above-described method for producing a semi-cured product.

The semi-cured product may not contain the photoradical polymerization initiator at all after the photoirradiation step, since the initiator is completely consumed in the step, or the photoradical polymerization initiator may remain in the semi-cured product.

In addition, the glass transition temperature (hereinafter, also referred to as "Tg") of the semi-cured product is preferably −150° C. to 0° C., more preferably −50° C. to 0° C., and particularly preferably −20° C. to 0° C.

(Method for Producing Cured Product)

The method for producing a cured product preferably includes a thermal polymerization step of putting the semi-cured product in a mold for pressure deformation therein, and heating it therein for thermal polymerization to give a cured product or a photopolymerizing step of photoirradiating the semi-cured product to give a cured product.

The method for producing a cured product preferably includes a step of subjecting the curable composition of the present invention to at least one of photoirradiation or heating to give a semi-cured product having a complex viscosity of $10^5$ to $10^8$ mPa·s at 25° C. and at a frequency of 10 Hz, and a polymerization step of putting the semi-cured product in a mold for pressure deformation therein and then subjecting the semi-cured product to at least one of photoirradiation or heating to give a cured product. The photoirradiation conditions and the heating conditions in the production step of a cured product are the same as those in the semi-curing step described above.

(Thermal Polymerization Step)

The mold used in the method for producing a cured product is also referred to as a thermal mold. In general, the thermal mold is composed of two mold parts and is preferably designed so that contents can be heated under pressure in the combination of the two mold parts. In the method for producing a cured product, a metal mold is more preferably used as the mold in the thermal polymerization step to obtain a cured product. The thermal mold of the type for use herein is described, for example, in JP2009-126011A.

(Introduction into Mold)

In the method for producing a cured product, first, the semi-cured product produced according to the semi-cured product production method is put into a mold. The semi-cured product after photoirradiation and/or heating is directly set in a thermal mold and is photoirradiated and/or heated therein, or is set in a mold different from a thermal mold and is photoirradiated and/or heated therein, as described in the section of Method for producing semi-cured product. In the case where the semi-cured product after photoirradiation is directly set in a thermal mold and is photoirradiated and/or heated therein, the operation of putting the semi-cured product into a thermal mold is unnecessary. On the other hand, in the case where the semi-cured product after photoirradiation and/or heating is set in a mold different from a thermal mold and is photoirradiated and/or heated therein, it is preferred to include a step of transferring the semi-cured product into a thermal mold. For the method of transferring the semi-cured product after photoirradiation and/or heating into a thermal mold, for example, an air tweezer equipped with a syringe, a vacuum pad, and a vacuum generator is usable. The semi-cured product has a complex viscosity falling within a specific range, and therefore can preferably be readily transferred into a thermal mold by the use of such an air tweezer.

(Pressure Deforming/Heating)

According to the method for producing a cured product, the semi-cured product put in a mold is deformed under pressure and heated for thermal polymerization to give a cured product. Here, pressure deforming and heating may be carried out simultaneously, or heating may be carried out after pressure deforming, or pressure deforming may be carried out after heating. Above all, preferably, pressure deforming and heating are carried out simultaneously. Also preferably, after simultaneous pressure deforming and heating, the product may be further heated at a higher temperature after the pressure applied thereto has become stable.

The pressure for the pressure deforming is preferably 0.098 MPa to 9.8 MPa, more preferably 0.294 MPa to 4.9 MPa, and particularly preferably 0.294 MPa to 2.94 MPa. In the case where the heating is carried out simultaneously with pressure deforming, the heating temperature is preferably 80° C. to 300° C., more preferably 120° C. to 300° C., and particularly preferably 150° C. to 280° C. On the other hand, in the case where the product is further heated at a higher temperature after the pressure applied thereto has become stable, the heating temperature is preferably 80° C. to 300° C., more preferably 120° C. to 300° C., and particularly preferably 150° C. to 280° C. The time of thermal polymerization is preferably 30 to 1,000 seconds, more preferably 30 to 500 seconds, and particularly preferably 60 to 300 seconds. The atmosphere during thermal polymerization is preferably in the air or after purging with an inert gas and more preferably an atmosphere purged with nitrogen until an oxygen concentration becomes 1% or less.

(Cured Product)

The present invention also relates to a cured product formed by curing a curable composition. The cured product of the present invention is preferably produced by the above-mentioned method for producing a cured product.

(Refractive Index)

The cured product of the present invention preferably has a high refractive index from the viewpoint of using it for optical components, especially for lenses. The refractive index nD at a wavelength of 589 nm of the cured product of the present invention is preferably 1.45 or more, more preferably 1.58 or more, more particularly preferably 1.60 or more, further particularly preferably 1.61 or more, and most preferably 1.62 or more.

(Abbe's Number)

The cured product of the present invention preferably has a low Abbe's number from the viewpoint of reducing the chromatic aberration in using it for optical components, especially for lenses. The cured product of the present invention has an Abbe's number of preferably 23 or less, more preferably 22.5 or less, particularly preferably 22 or less, and still more particularly preferably 21.6 or less.

In the present specification, the Abbe's number vD is calculated according to the following expression by measuring refractive indices nD, nF and nC at wavelengths of 589 nm, 486 nm and 656 nm, respectively, using an Abbe meter (manufactured by Atago Co., Ltd.).

$$vD=(nD-1)/(nF-nC)$$

In the expression, nD, nF and nC each are a refractive index at a wavelength of 589 nm, 486 nm and 656 nm, respectively.

(Size)

The maximum thickness of the cured product of the present invention is preferably 0.1 to 10 mm. The maximum thickness is more preferably 0.1 to 5 mm and particularly preferably 0.15 to 3 mm. The maximum diameter of the cured product of the present invention is preferably 1 to 1,000 mm. The maximum diameter is more preferably 2 to 200 mm and particularly preferably 2.5 to 100 mm. The cured product having the size as above is especially useful for optical components having a high refractive index. In general, it is not easy to produce such a thick molded article according to a solution casting method since the solvent is difficult to remove, or that is, molding the article is not easy. However, the use of the curable composition of the present invention makes it easy to mold such a thick molded article and provides high handleability, whereby a cured product of high quality can be obtained.

(Optical Components)

The present invention also relates to an optical component including the above-mentioned cured product. Since the cured product of the present invention is a molded article having high refractivity, high light transmittance, lightweightness and excellent optical properties, it is preferably used as an optical component. The type of the optical component of the present invention is not particularly limited. In particular, the cured product of the present invention is favorably used for optical components that utilize the excellent optical properties of curable compositions, especially for light-transmissive optical components (so-called passive optical components). Examples of optically-functional devices equipped with such optical components include various types of display devices (a liquid crystal display, a plasma display, and the like), various types of projector devices (an overhead projector (OHP), a liquid crystal projector, and the like), optical fiber communication systems (a light waveguide, a light amplifier, and the like), and image-taking devices such as a camera and a video.

Examples of the passive optical components for use in optically-functional devices include lenses, prisms, prism sheets, panels (plate-like molded articles), films, optical waveguides (film-like optical waveguide, a fiber-like optical waveguide, and the like), optical discs, and LED sealants. If desired, the passive optical components may be provided with an optional coating layer, such as a protective layer for preventing mechanical damage of the coating surface by friction or abrasion, a light-absorbing layer for absorbing the light having an undesirable wavelength to cause degradation of inorganic particles, substrates and others, a blocking layer for retarding or preventing permeation of reactive small molecules such as moisture or oxygen gas, an antiglare layer, an antireflection layer, a layer of low refractive index, or the like, as well as any additional functional layer. Specific examples of the optional coating layer include a transparent conductive film or gas-barrier layer formed of an inorganic oxide coating layer, and a gas-barrier layer or hard coat layer formed of an organic coating layer. The coating method for these layers may be any known coating method such as a vacuum deposition method, a chemical vapor deposition (CVD) method, a sputtering method, a dip coating method, or a spin coating method.

Application Examples

The optical component using the cured product of the present invention is especially favorable for a lens substrate. The lens substrate produced using the curable composition of the present invention has a low Abbe's number and preferably has high refractivity, high light transmittance and lightweightness and is excellent in optical properties. By suitably adjusting the type of monomer constituting the curable composition, it is possible to control the refractive index of the lens substrate in any desired manner.

In addition, in the present specification, the "lens substrate" refers to a single component capable of exhibiting a lens function. On and around the surface of the lens substrate, any film and component may be provided in accordance with the usage environment and intended purpose of lenses. For example, on the surface of the lens substrate, a protective film, an antireflection film, a hard coat film, or the like may be formed. Further, it can be a composite lens in which a glass lens substrate or a plastic lens substrate is laminated. It is also possible to make the periphery of the lens substrate intrude and be fixed in a substrate holding frame. However, those films and frames are additional components to the lens substrate and therefore differ from the lens substrate itself referred to in the present specification.

In the case of using the lens substrate for lenses, the lens substrate itself may be used as a lens by itself, or additional films or frames or additional lens substrates may be added thereto for use as a lens, as mentioned above. The type and the shape of the lens using the lens substrate are not particularly limited.

The lens substrate has a low Abbe's number and is therefore preferably used for an achromatic lens, and the achromatic lens is used, for example, for lenses for imaging devices such as mobile phones or digital cameras; lenses for movie devices such as TV or video cameras; and lenses for in-vehicle devices or endoscope lenses.

EXAMPLES

Hereinafter, the features of the present invention will be more specifically described with reference to Examples and Comparative Examples. In the following Examples, the materials to be used, amounts and ratios thereof, the details of the treatment and the treatment procedures, and the like may be suitably modified or changed without departing from the scope of the present invention. Accordingly, the scope of the present invention should not be limitedly interpreted by the following specific Examples.

(Synthesis of Compound)

<Synthesis of Compound 2-1>

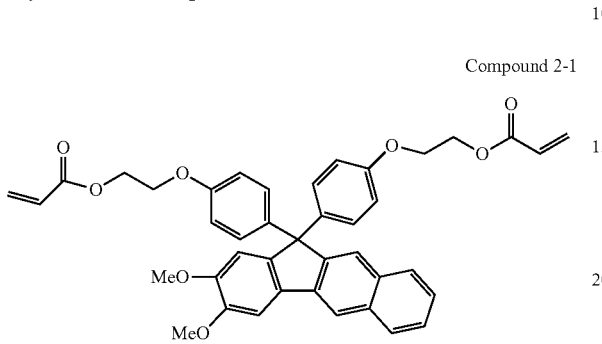

Compound 2-1

The Compound 2-1 was synthesized by the following method.

290 g of 5,6-dimethoxy-1-indanone and 204 g of ortho-phthalaldehyde were dissolved in 1,500 mL of methanol. The reaction solution was warmed, and 255 g of potassium hydroxide dissolved in 1,750 mL of methanol was added dropwise thereto while maintaining the temperature at 60° C. After stirring for 5 hours, the reaction solution was returned to room temperature, and the precipitated crystals were collected by filtration to give 230 g of Compound 2-1A.

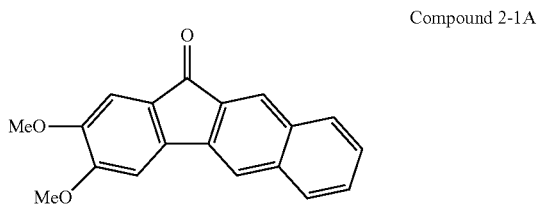 [SMILES: COc1cc2c(cc1OC)-c1cc3ccccc3cc1C2=O]

Compound 2-1A 200 g of Compound 2-1A and 320 g of phenol were dissolved in 320 mL of methane sulfonic acid. The reaction solution was warmed and 3.2 mL of 3-mercaptopropionic acid was added dropwise thereto while maintaining the temperature at 60° C. After stirring for 5 hours, 720 mL of methanol was added dropwise to the reaction solution. After stirring for 30 minutes, 1,400 mL of methanol was further added dropwise thereto. The reaction solution was returned to room temperature, and the precipitated crystals were collected by filtration to give 292 g of Compound 2-1B. $^1$H-NMR data are shown in FIG. 1.

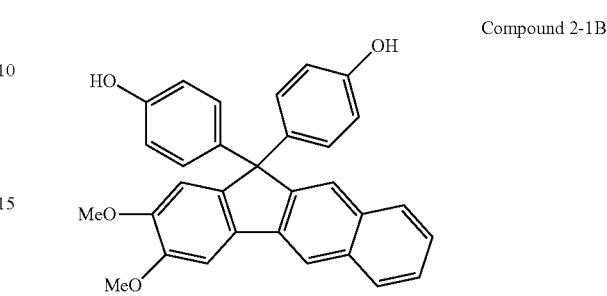

Compound 2-1B 132 mL of triethylamine and 650 mL of butyl acetate were added to 100 g of 2-hydroxyethyl acrylate, followed by stirring. While maintaining the reaction solution at 5° C., 70 mL of methane sulfonic acid chloride was added dropwise over 1 hour. After stirring for 1 hour, 500 mL of water was added to the reaction solution which was then stirred, and the operation of removing the water layer was repeated three times. 30 mg of dibutylhydroxytoluene was added and then butyl acetate was distilled off under reduced pressure to give 160 g of Compound 2-1C.

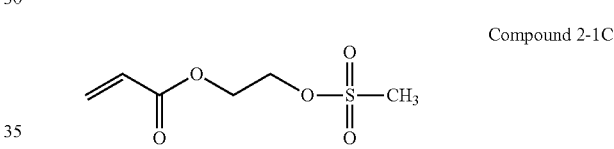

Figure 2:
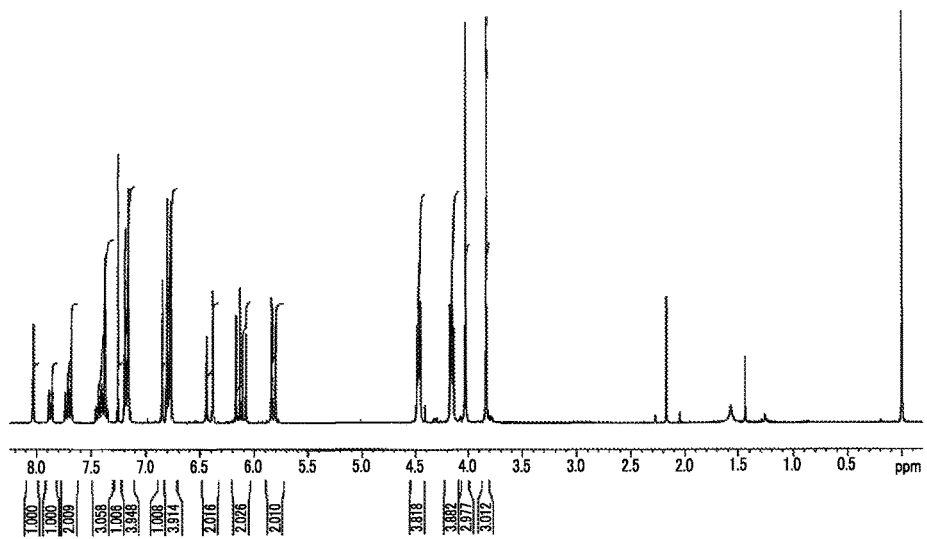
FIG. 2 is a $^1$H-NMR chart of Compound 2-1.

Compound 2-1C 500 mL of butyl acetate, 0.5 mL of nitrobenzene, 138 g of potassium carbonate, and 8 g of tetrabutylammonium bromide (TBAB) were added to 100 g of Compound 2-1B, followed by stirring. 150 g of Compound 2-1C was added to the reaction solution, followed by reacting for 5 hours while maintaining the temperature at 80° C., and 250 mL of toluene was added thereto, followed by stirring. 300 mL of water was added to the reaction solution which was then stirred while maintaining the temperature at 60° C., and the operation of removing the water layer was repeated three times. The residue was purified by column chromatography to give 120 g of Compound 2-1. $^1$H-NMR data are shown in FIG. 2.

<Synthesis of Compound 2-2>

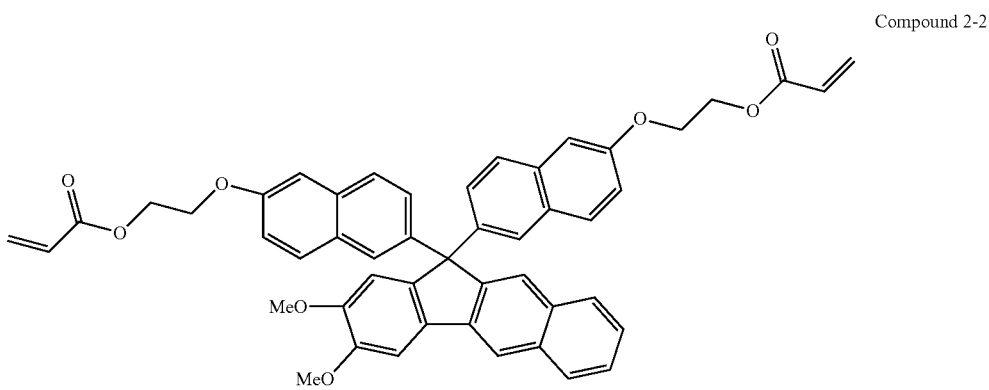 [SMILES: C=CC(=O)OCCOc1ccc2cc(C3(c4ccc5cc(OCCOC(=O)C=C)ccc5c4)c4cc(OC)c(OC)cc4-c4cc5ccccc5cc43)ccc2c1]

Compound 2-2

The Compound 2-2 was synthesized by the following method.

230 g of Compound 2-1A and 160 g of Compound 2-1C were obtained in the same manner as in Compound 2-1. 250 g of 2-naphthol, 300 mL of toluene, and 320 mL of methane sulfonic acid were added to 200 g of Compound 2-1A, followed by stirring. The reaction solution was warmed, and 3.2 mL of 3-mercaptopropionic acid was added dropwise thereto while maintaining the temperature at 60° C. After reacting for 3 hours, 320 mL of methanol was added dropwise to the reaction solution which was then stirred for 30 minutes, and 1,400 mL of methanol was further added thereto. The reaction solution was returned to room temperature, and the precipitated crystals were collected by filtration to give 220 g of Compound 2-2B.

Compound 2-2B

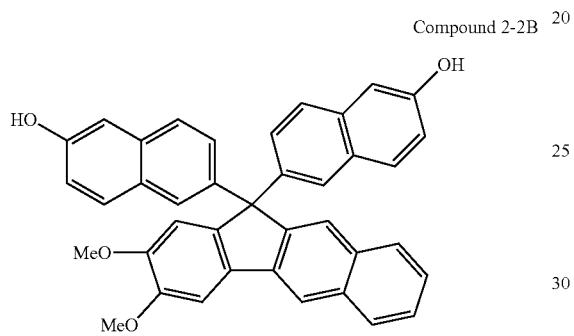

500 mL of butyl acetate, 0.5 mL of nitrobenzene, 138 g of potassium carbonate, and 8 g of tetrabutylammonium bromide (TBAB) were added to 100 g of Compound 2-2B, followed by stirring. 150 g of Compound 2-1C was added to the reaction solution, followed by reacting for 5 hours while maintaining the temperature at 80° C., and then 250 mL of toluene was added thereto, followed by stirring. 300 mL of water was added to the reaction solution which was then stirred while maintaining the temperature at 60° C., and the operation of removing the water layer was repeated three times. The residue was purified by column chromatography to give 120 g of Compound 2-2.

<Synthesis of Compound 2-3>

The Compound 2-3 was synthesized by the following method.

292 g of Compound 2-1B was obtained in the same manner as in Compound 2-1. 106 mL of triethylamine and 790 mL of butyl acetate were added to 100 g of 4-hydroxybutyl acrylate, followed by stirring. While maintaining the reaction solution at 5° C., 56 mL of methane sulfonic acid chloride was added dropwise thereto over 1 hour. After stirring for 1 hour, 500 mL of water was added to the reaction solution which was then stirred, and the operation of removing the water layer was repeated three times. 30 mg of dibutylhydroxytoluene was added, and butyl acetate was distilled off under reduced pressure to give 145 g of Compound 2-3C.

Compound 2-3C

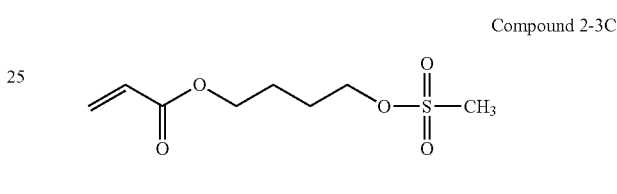

Figure 3:
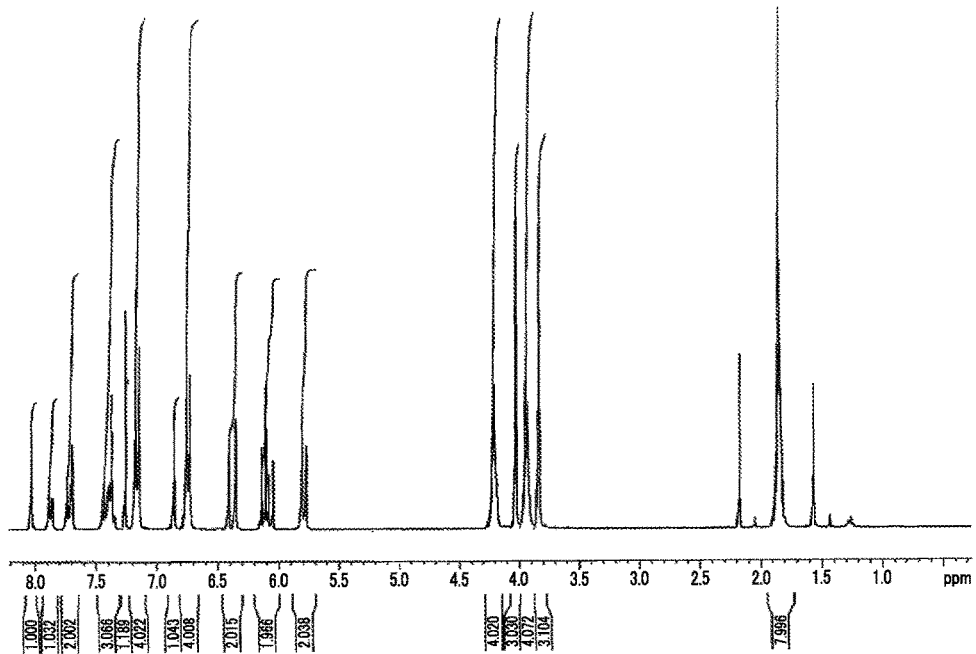
FIG. 3 is a $^1$H-NMR chart of Compound 2-3.

500 mL of butyl acetate, 0.5 mL of nitrobenzene, 138 g of potassium carbonate, and 8 g of tetrabutylammonium bromide (TBAB) were added to 100 g of Compound 2-1B, followed by stirring. 130 g of Compound 2-3C was added to the reaction solution, followed by reacting for 5 hours while maintaining the temperature at 80° C., and then 250 mL of toluene was added thereto, followed by stirring. 300 mL of water was added to the reaction solution which was then stirred while maintaining the temperature at 60° C., and the operation of removing the water layer was repeated three times. The residue was purified by column chromatography to give 130 g of Compound 2-3. $^1$H-NMR data are shown in FIG. 3.

Compound 2-3

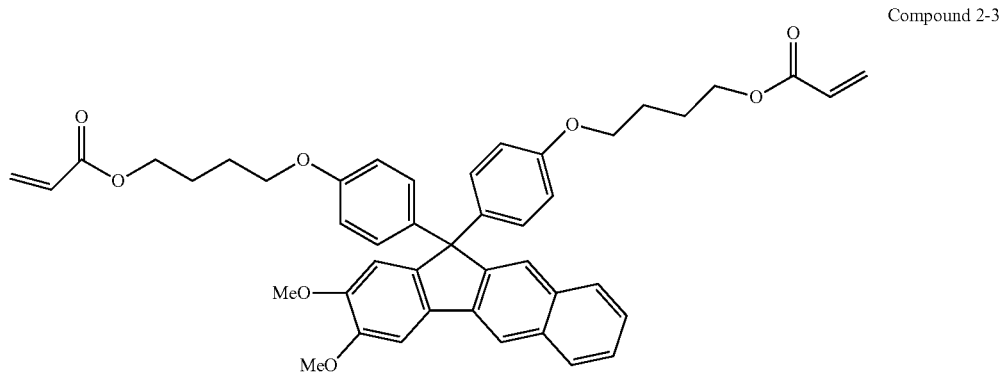 [SMILES: C=CC(=O)OCCCCOc1ccc(C2(c3ccc(OCCCCOC(=O)C=C)cc3)c3cc(OC)c(OC)cc3-c3cc4ccccc4cc32)cc1]

<Synthesis of Compound 2-4>

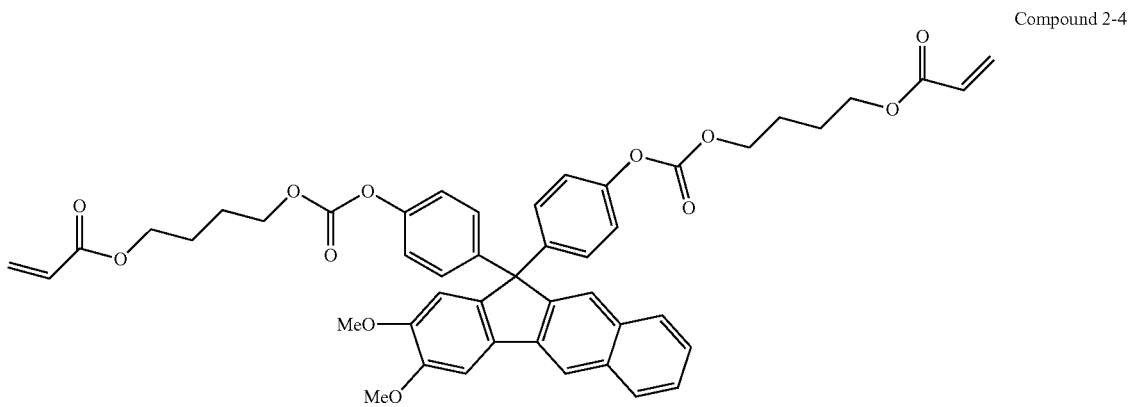 [SMILES: C=CC(=O)OCCCCOC(=O)Oc1ccc(C2(c3ccc(OC(=O)OCCCCOC(=O)C=C)cc3)c3cc(OC)c(OC)cc3-c3cc4ccccc4cc32)cc1]

Compound 2-4

The Compound 2-4 was synthesized by the following method.

292 g of Compound 2-1B was obtained in the same manner as in Compound 2-1.

1,400 mL of ethyl acetate was added to 200 g of 4-hydroxybutyl acrylate, followed by stirring. While maintaining the reaction solution at 5° C., 183 mL of triphosgene and 265 mL of N,N'-diethylaniline were added dropwise thereto over 2 hours. After stirring for 1 hour, 500 mL of water was added to the reaction solution which was then stirred, and the operation of removing the water layer was repeated three times. 30 mg of dibutylhydroxytoluene was added and then ethyl acetate was distilled off under reduced pressure to give 273 g of Compound 2-4C.

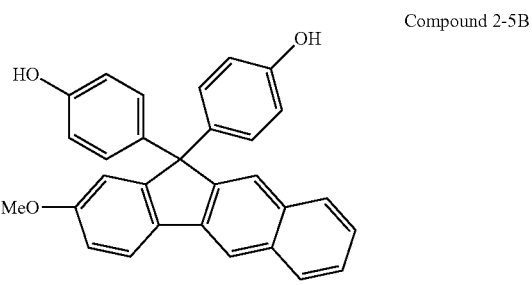 [SMILES: COc1ccc2c(c1)C(c1ccc(O)cc1)(c1ccc(O)cc1)c1cc3ccccc3cc1-2]

Compound 2-4C 1,000 mL of tetrahydrofuran and 110 g of triethylamine were added to 100 g of Compound 2-1B, followed by stirring. While maintaining the reaction solution at 5° C., 136 g of Compound 2-4C was added thereto over hours, followed by reacting for 1 hour and then reacting at 25° C. for another 1 hour. 700 mL of water and 650 mL of ethyl acetate were added to the reaction solution which was then stirred, and the operation of removing the water bath was repeated three times. Ethyl acetate contained in the residue was removed under reduced pressure, and 500 mL of methanol and 500 mL of water were added. This was followed by stirring while maintaining the temperature at 5° C., so that crystals were precipitated to give 116 g of Compound 2-4.

<Synthesis of Compound 2-5>

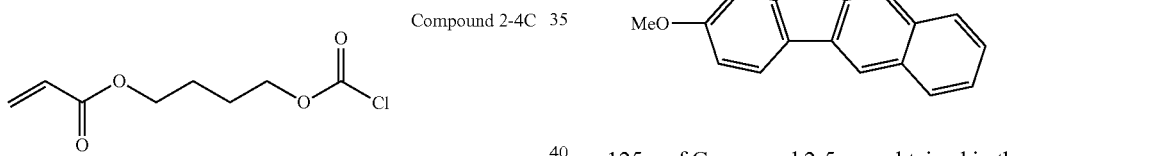

Compound 2-5

Figure 4:
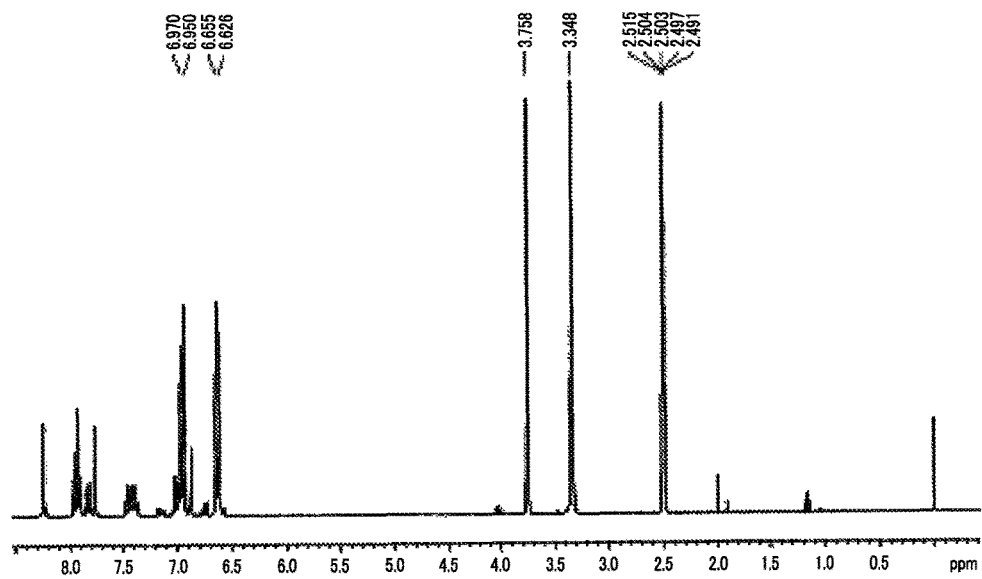
FIG. 4 is a $^1$H-NMR chart of Compound 2-5B.

The Compound 2-5 was synthesized by the following method. 260 g of Compound 2-5B was obtained in the same manner as in the synthesis of Compound 2-1, except that 6-methoxy-1-indanone was used in place of 5,6-dimethoxy-1-indanone. $^1$H-NMR data are shown in FIG. 4.

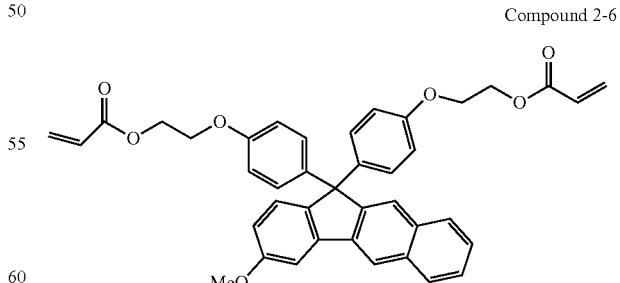

Figure 5:
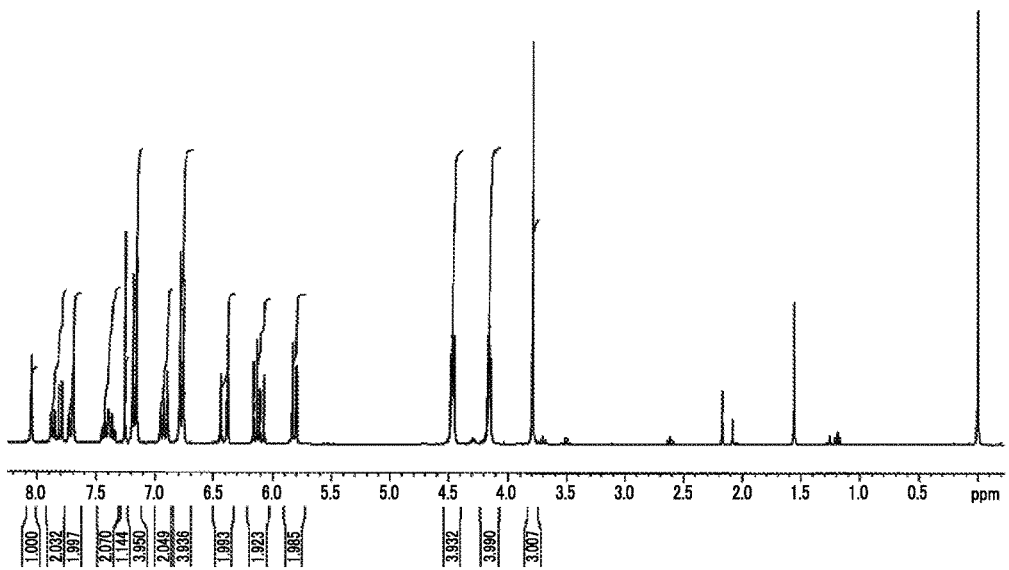
FIG. 5 is a $^1$H-NMR chart of Compound 2-5.

Compound 2-5B 125 g of Compound 2-5 was obtained in the same manner as in the synthesis of Compound 2-1, except that Compound 2-5B was used in place of Compound 2-1B. $^1$H-NMR data are shown in FIG. 5.

<Synthesis of Compound 2-6>

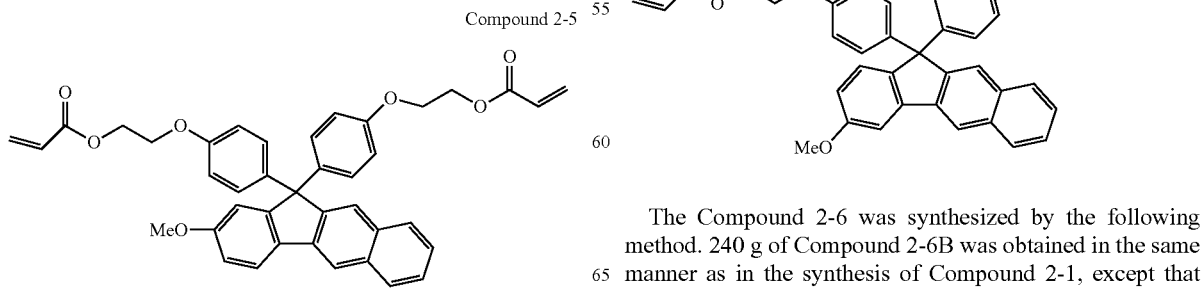

Compound 2-6

Figure 6:
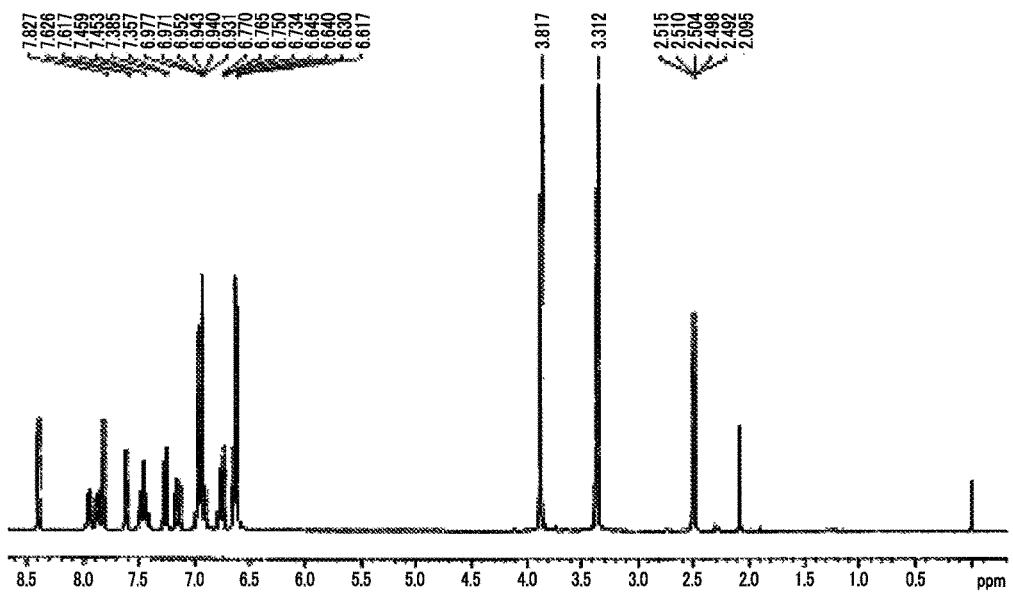
FIG. 6 is a $^1$H-NMR chart of Compound 2-6B.

The Compound 2-6 was synthesized by the following method. 240 g of Compound 2-6B was obtained in the same manner as in the synthesis of Compound 2-1, except that 5-methoxy-1-indanone was used in place of 5,6-dimethoxy-1-indanone. $^1$H-NMR data are shown in FIG. 6.

Compound 2-6B

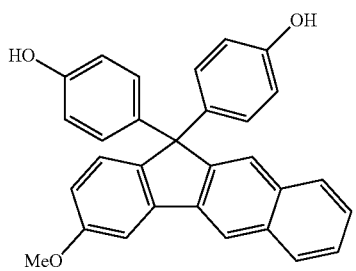

Figure 7:
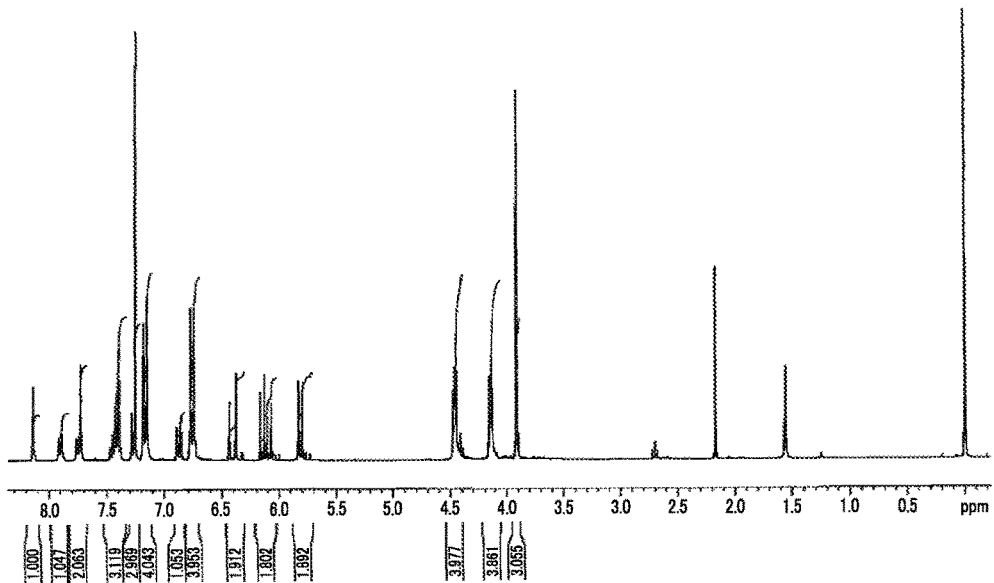
FIG. 7 is a $^1$H-NMR chart of Compound 2-6.

115 g of Compound 2-6 was obtained in the same manner as in the synthesis of Compound 2-1, except that Compound 2-6B was used in place of Compound 2-1B. $^1$H-NMR data are shown in FIG. 7.

<Synthesis of Compound 2-7>

Compound 2-7

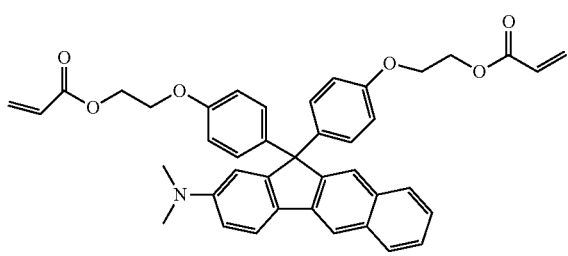

115 g of Compound 2-7 was obtained in the same manner as in the synthesis of Compound 2-1, except that 6-dimethylamino-1-indanone was used in place of 5,6-dimethoxy-1-indanone.

<Synthesis of Compound 2-8>

Compound 2-8

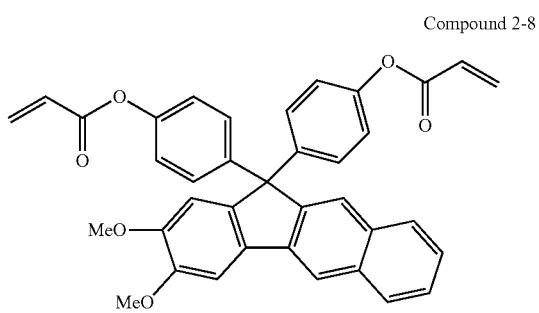 [SMILES: C=CC(=O)Oc1ccc(C2(c3ccc(OC(=O)C=C)cc3)c3cc(OC)c(OC)cc3-c3cc4ccccc4cc32)cc1]

The Compound 2-8 was synthesized by the following method.

Figure 8:
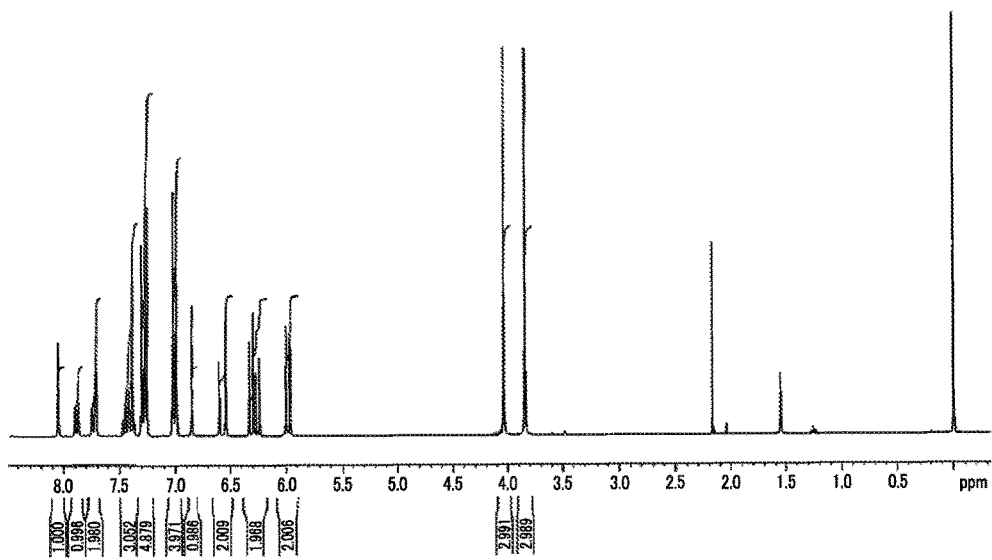
FIG. 8 is a $^1$H-NMR chart of Compound 2-8.

292 g of Compound 2-1B was obtained in the same manner as in Compound 2-1. 500 mL of tetrahydrofuran and 72 g of diisopropylethylamine were added to 100 g of Compound 2-1B, followed by stirring. While maintaining the reaction solution at 5° C., 49 g of acryloyl chloride wad added thereto over 1 hour, followed by reacting for 1 hour and then reacting at 25° C. for another 1 hour. 700 mL of water and 650 mL of ethyl acetate were added to the reaction solution which was then stirred, and the operation of removing the water bath was repeated three times. Ethyl acetate contained in the residue was removed under reduced pressure and then 1,000 mL of methanol was added, followed by stirring, so that crystals were precipitated to give 132 g of Compound 2-8. $^1$H-NMR data are shown in FIG. 8.

<Synthesis of Compound 2-9>

Compound 2-9

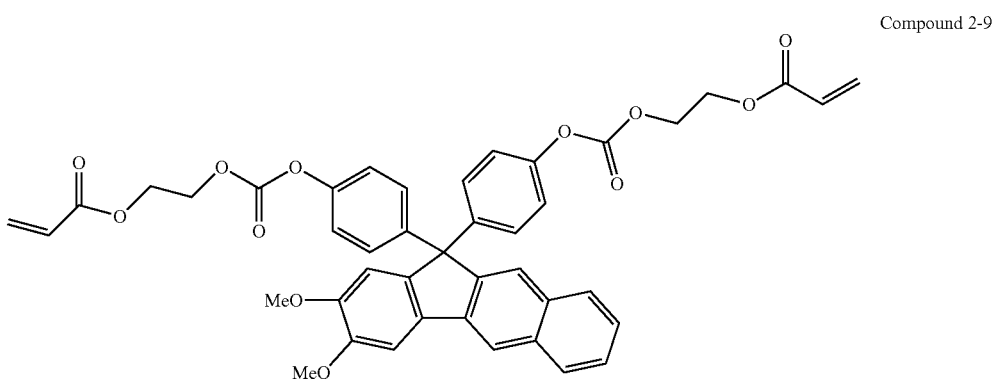 [SMILES: C=CC(=O)OCCOC(=O)Oc1ccc(C2(c3ccc(OC(=O)OCCOC(=O)C=C)cc3)c3cc(OC)c(OC)cc3-c3cc4ccccc4cc32)cc1]

The Compound 2-9 was synthesized by the following method.

292 g of Compound 2-1B was obtained in the same manner as in Compound 2-1.

1,400 mL of ethyl acetate was added to 200 g of 2-hydroxyethyl acrylate, followed by stirring. While maintaining the reaction solution at 5° C., 212 mL of triphosgene and 308 mL of N,N'-diethylaniline were added dropwise thereto over 2 hours. After stirring for 1 hour, 500 mL of water was added to the reaction solution which was then stirred, and the operation of removing the water layer was repeated three times. 30 mg of dibutylhydroxytoluene was added and then ethyl acetate was distilled off under reduced pressure to give 293 g of Compound 2-9C.

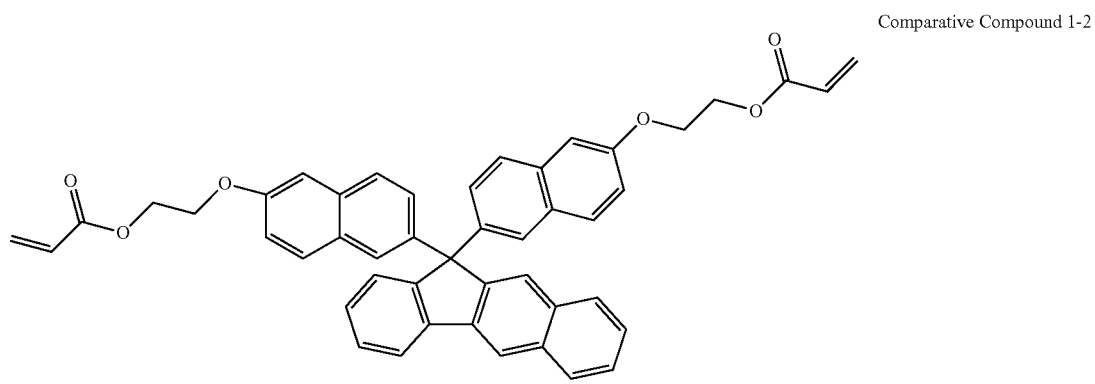 [SMILES: C=CC(=O)OCCOc1ccc2cc(C3(c4ccc5cc(OCCOC(=O)C=C)ccc5c4)c4ccccc4-c4cc5ccccc5cc43)ccc2c1]

Figure 9:
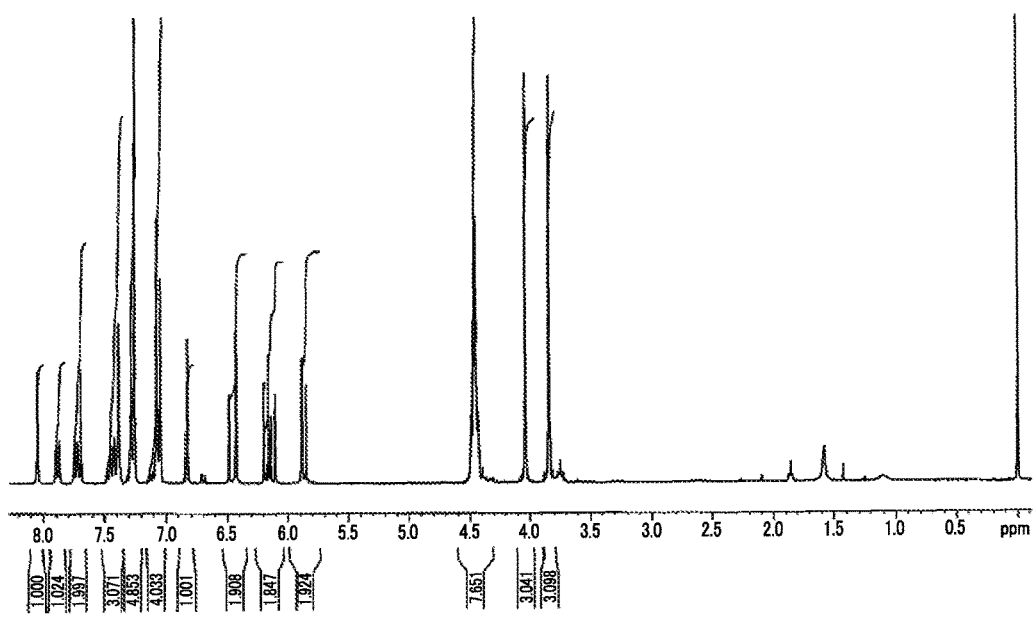
FIG. 9 is a $^1$H-NMR chart of Compound 2-9.

Compound 2-9C 1,000 mL of tetrahydrofuran and 110 g of triethylamine were added to 100 g of Compound 2-1B, followed by stirring. While maintaining the reaction solution at 5° C., 117 g of Compound 2-9C was added thereto over 1 hour, followed by reacting for 1 hour and then reacting at 25° C. for another 1 hour. 700 mL of water and 650 mL of ethyl acetate were added to the reaction solution which was then stirred, and the operation of removing the water bath was repeated three times. Ethyl acetate contained in the residue was removed under reduced pressure, and 500 mL of methanol and 500 mL of water were added, followed by stirring while maintaining the temperature at 5° C., so that crystals were precipitated to give 113 g of Compound 2-9. $^1$H-NMR data are shown in FIG. 9.

<Synthesis of Comparative Compound 1-1>

Comparative Compound 1-1

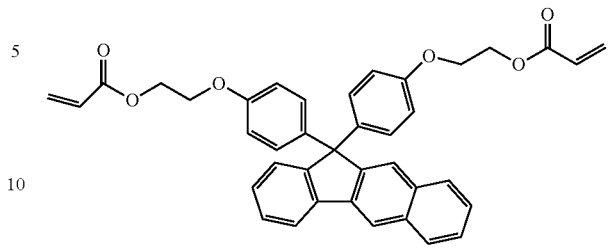

Comparative Compound 1-1 was synthesized according to the synthesis method described in Example 1 of JP2014-80572A.

<Synthesis of Comparative Compound 1-2>

Comparative Compound 1-2

Comparative Compound 1-2 was synthesized according to the synthesis method described in paragraph "0133" of JP2014-80572A.

<Synthesis of Comparative Compound 1-3>

Comparative Compound 1-3

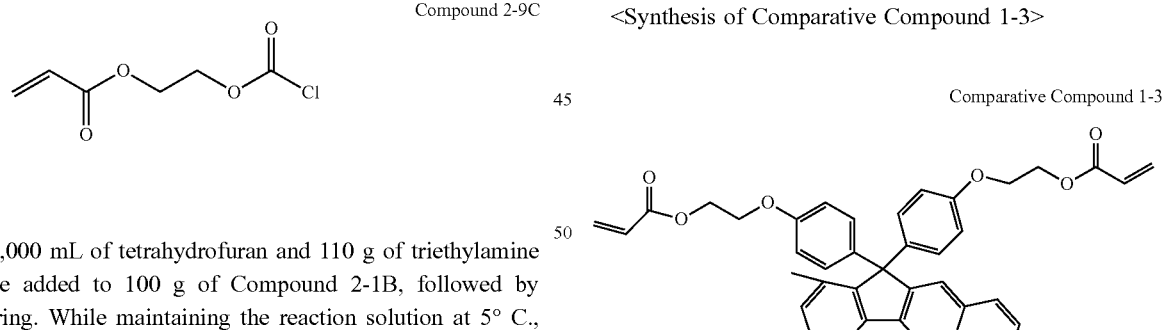

The Comparative Compound 1-3 was synthesized by the following method.

290 g of 7-methyl-1-indanone and 204 g of ortho-phthalaldehyde were dissolved in 1,500 mL of methanol. The reaction solution was warmed, and 255 g of potassium hydroxide dissolved in 1,750 mL of methanol was added dropwise thereto while maintaining the temperature at 60° C. After stirring for 5 hours, the reaction solution was returned to room temperature, and the precipitated crystals were collected by filtration to give 220 g of Compound 1-3A.

Compound 1-3A 200 g of Compound 1-3A and 320 g of phenol were dissolved in 320 mL of methane sulfonic acid. The reaction solution was warmed, and 3.2 mL of 3-mercaptopropionic acid was added dropwise thereto while maintaining the temperature at 60° C. After stirring for 5 hours, 720 mL of methanol was added dropwise to the reaction solution which was then stirred for 30 minutes, and 1,400 mL of methanol was further added dropwise thereto. The reaction solution was returned to room temperature, and the precipitated crystals were collected by filtration to give 294 g of Compound 1-3B.

Compound 1-3B 132 mL of triethylamine and 650 mL of butyl acetate were added to 100 g of 2-hydroxyethyl acrylate, followed by stirring. While maintaining the reaction solution at 5° C., 70 mL of methane sulfonic acid chloride was added dropwise thereto over 1 hour. After stirring for 1 hour, 500 mL of water was added to the reaction solution which was then stirred, and the operation of removing the water layer was repeated three times. 30 mg of dibutylhydroxytoluene was added and then butyl acetate was distilled off under reduced pressure to give 160 g of Compound 1-3C.

Compound 1-3C 500 mL of butyl acetate, 0.5 mL of nitrobenzene, 138 g of potassium carbonate, and 8 g of tetrabutylammonium bromide (TBAB) were added to 100 g of Compound 1-3B, followed by stirring. 150 g of Compound 1-3C was added to the reaction solution, followed by reacting for 5 hours while maintaining the temperature at 80° C., and then 250 mL of toluene was added, followed by stirring. 300 mL of water was added to the reaction solution which was then stirred while maintaining the temperature at 60° C., and the operation of removing the water layer was repeated three times. The residue was purified by column chromatography to give 120 g of Comparative Compound 1-3.

Examples 1 to 17 and Comparative Examples 1 to 6

The above-mentioned compounds and the following components were added so as to obtain the compositions described in the following Tables 1 and 2, and the mixtures were stirred to homogeneity to prepare the curable compositions.

<(Meth)Acrylic Monomer>

The following compounds were used as the (meth)acrylic monomer.

Monomer 1: manufactured by Osaka Organic Chemical Industry Ltd., product name: VISCOAT #192 PEA (viscosity at 25° C. and shear rate of 10 s$^{-1}$: 9 mPa·s)

Monomer 2: manufactured by Osaka Organic Chemical Industry Ltd., product name: VISCOAT #160 BZA (viscosity at 25° C. and shear rate of 10 s$^{-1}$: 8 mPa·s)

Monomer 3: manufactured by Shin-Nakamura Chemical Co., Ltd., product name: A-DCP (viscosity at 25° C. and shear rate of 10 s$^{-1}$: 120 mPa·s)

Monomer 4: manufactured by Hitachi Chemical Co., Ltd., product name: FA-513AS (viscosity at 25° C. and shear rate of 10 s$^{-1}$: 12 mPa·s)

Monomer 1

Monomer 2

Monomer 3

Monomer 4

<Non-Conjugated Vinylidene Group-Containing Compound>

The following compound (manufactured by Inoue Perfumery Co., Ltd., β-caryophyllene) was used as the non-conjugated vinylidene group-containing compound. There is no particular restriction on the optical isomers.

<Photoradical Polymerization Initiator>

The following compound (manufactured by BASF Corp., Irgacure 651) was used as the photoradical polymerization initiator.

Irgacure 651

<Thermal Radical Polymerization Initiator>

The following compounds were used as the thermal radical polymerization initiator.
PERBUTYL O: manufactured by NOF Corporation
PERCUMYL H-80: manufactured by NOF Corporation

PERBUTYL O

PERCUMYL H-80

(Evaluation)
<Viscosity of (Meth)Acrylate Monomer>

Measurement was carried out using a rheometer (RS 600) manufactured by HAAKE GmbH under conditions of 25° C. and a shear rate of 10 s$^{-1}$.

<Viscosity of Curable Composition>

The viscosities of the curable compositions obtained in Examples and Comparative Examples were measured using a rheometer (RS 600) manufactured by HAAKE GmbH under conditions of 25° C. and a shear rate of 10 s$^{-1}$.

<Abbe's Number>

The curable compositions obtained in Examples and Comparative Examples were respectively injected into a transparent glass mold having a diameter of 10 mm and a thickness of 1 mm and heated to 200° C. in an atmosphere having an oxygen concentration of 1% or less to prepare thermally cured products. The Abbe's number (νD) of the obtained thermally cured products was measured using an Abbe meter (manufactured by Atago Co., Ltd.).

$$\nu D = (nD-1)/(nF-nC)$$

in which nD, nF and nC are each a refractive index at a wavelength of 589 nm, 486 nm and 656 nm, respectively.

Although thermally cured products were used for the measurement of the Abbe's number, the Abbe's number was unchanged even for cured products subjected to thermal curing after ultraviolet irradiation.

<Crack Resistance (Durability)>

200 mg of each of the curable compositions obtained in Examples and Comparative Examples was poured between a mold whose surface was treated with chromium nitride and a glass lens which was surface-treated with acryloyloxypropyltrimethoxysilane (glass material: S-BSL7 (manufactured by OHARA Inc.), a convex lens having a diameter of 33 mm, a center thickness of 3 mm, a curvature radius of 44.3 mm on the surface in contact with the curable composition and a curvature radius of 330.9 mm on the surface not in contact with the curable composition), and then the diameter of the curable composition was adjusted to 30 mm. After this state, ultraviolet rays of 300 mJ/cm$^2$ were irradiated from above the glass lens using Execure 3000 (manufactured by HOYA Corporation). Then, the temperature was raised to 200° C. while applying a pressure of 0.196 MPa (2 kgf/cm$^2$) to the curable composition while being sandwiched between the mold and the glass lens, and the cured product of the curable composition and the mold were separated at a rate of 0.05 mm/sec to prepare a cured product laminated on the glass lens. The cured product was placed in a constant-temperature tank kept at −40° C. and the time until cracking occurred was measured.

<Substituent Constant $\sigma_p$ Value of Compound>

In Compounds 2-1 to 2-9 and Comparative Compounds 1-1 to 1-3, the values described in Correlation Analysis in Chemistry, Ed. By N. B. Chapman, J. Shorter, pp 439 to 540, Plenum Press (1978) were used as substituent constant $\sigma_p$ values of the substituents which are disposed at positions corresponding to R$^1$ to R$^4$ in General Formula (A). Note that a, is a Hammett substituent constant determined from the following equation, and up is defined as follows.

$$\sigma_p = \mathrm{Log}(Ka/Ka^0) = pKa^0 - pKa$$

in which Ka$^0$ is an acid dissociation constant of benzoic acid in water at 25° C., and Ka is an acid dissociation constant of para-substituted benzoic acid in water at 25° C.

TABLE 1

| | | Example 1 | Example 2 | Example 3 | Example 4 | Example 5 | Example 6 | Example 7 | Example 8 | Example 9 |
|---|---|---|---|---|---|---|---|---|---|---|
| Compound | Comparative Compound 1-1 | | | | | | | | | |
| | Comparative Compound 1-2 | | | | | | | | | |
| | Comparative Compound 1-3 | | | | | | | | | |
| | Compound 2-1 | 67.5 | 67.5 | | | | | 70 | 70 | |
| | Compound 2-2 | | | 55 | | | | | | |
| | Compound 2-3 | | | | 80 | | | | | |
| | Compound 2-4 | | | | | 85 | | | | |
| | Compound 2-5 | | | | | | 67.5 | | | |
| | Compound 2-6 | | | | | | | | | 67.5 |
| | Compound 2-7 | | | | | | | | | |
| | Compound 2-8 | | | | | | | | | |
| | Compound 2-9 | | | | | | | | | |

TABLE 1-continued

| | | | | | | | | | | |
|---|---|---|---|---|---|---|---|---|---|---|
| | Substituent constant σ$_p$ values of R$^1$ to R$^4$ | −0.28 | −0.28 | −0.28 | −0.28 | −0.28 | −0.28 | −0.28 | −0.28 | −0.28 |
| (Meth)acrylate monomer | Monomer 1 | 26.2 | | 38.7 | 13.7 | 8.7 | 26.2 | | | 26.2 |
| | Monomer 2 | | 26.2 | | | | | | | |
| | Monomer 3 | | | | | | | 23.7 | | |
| | Monomer 4 | | | | | | | | 23.7 | |
| Non-conjugated vinylidene group-containing compound | β-caryophyllene | 4.5 | 4.5 | 4.5 | 4.5 | 4.5 | 4.5 | 4.5 | 4.5 | 4.5 |
| Photoradical polymerization initiator | Irgacure 651 | 0.1 | 0.1 | 0.1 | 0.1 | 0.1 | 0.1 | 0.1 | 0.1 | 0.1 |
| Thermal radical polymerization initiator | PERBUTYL O | 1 | 1 | 1 | 1 | 1 | 1 | 1 | 1 | 1 |
| | PERCUMYL H-80 | 0.7 | 0.7 | 0.7 | 0.7 | 0.7 | 0.7 | 0.7 | 0.7 | 0.7 |
| Evaluation of curable resin composition | Viscosity (mPa · s) | 11,500 | 7,500 | 9,800 | 11,500 | 11,800 | 12,000 | 11,500 | 6,500 | 12,600 |
| Evaluation of cured product | Abbe's number | 20.8 | 20.5 | 20.8 | 21.2 | 21.5 | 21.4 | 21.5 | 21.4 | 22.1 |
| | Crack resistance (time (h) until cracks occurred after storage at −40° C.) | 1400 | 700 | 750 | 820 | 650 | 400 | 350 | 240 | 650 |

| | | Example 10 | Example 11 | Example 12 | Comparative Example 1 | Comparative Example 2 | Comparative Example 3 | Comparative Example 4 | Comparative Example 5 | Comparative Example 6 |
|---|---|---|---|---|---|---|---|---|---|---|
| Compound | Comparative Compound 1-1 | | | | 67.5 | 80 | 80 | | | |
| | Comparative Compound 1-2 | | | | | | | 67.5 | 67.5 | |
| | Comparative Compound 1-3 | | | | | | | | | 67.5 |
| | Compound 2-1 | | | | | | | | | |
| | Compound 2-2 | | | | | | | | | |
| | Compound 2-3 | | | | | | | | | |
| | Compound 2-4 | | | | | | | | | |
| | Compound 2-5 | | | | | | | | | |
| | Compound 2-6 | | | | | | | | | |
| | Compound 2-7 | 65 | | | | | | | | |
| | Compound 2-8 | | 60 | | | | | | | |
| | Compound 2-9 | | | 65 | | | | | | |
| | Substituent constant σ$_p$ values of R$^1$ to R$^4$ | −0.63 | −0.28 | −0.63 | 0 | 0 | 0 | 0 | 0 | −0.06 |
| (Meth)acrylate monomer | Monomer 1 | 28.7 | 33.7 | 26.7 | 26.2 | 13.7 | | 26.2 | | 26.2 |
| | Monomer 2 | | | | | | 13.7 | | 26.2 | |
| | Monomer 3 | | | | | | | | | |
| | Monomer 4 | | | | | | | | | |
| Non-conjugated vinylidene group-containing compound | β-caryophyllene | 4.5 | 4.5 | 4.5 | 4.5 | 4.5 | 4.5 | 4.5 | 4.5 | 4.5 |
| Photoradical polymerization initiator | Irgacure 651 | 0.1 | 0.1 | 0.1 | 0.1 | 0.1 | 0.1 | 0.1 | 0.1 | 0.1 |
| Thermal radical polymerization initiator | PERBUTYL O | 1 | 1 | 1 | 1.0 | 1 | 1 | 1 | 1 | 1 |
| | PERCUMYL H-80 | 0.7 | 0.7 | 0.7 | 0.7 | 0.7 | 0.7 | 0.7 | 0.7 | 0.7 |
| Evaluation of curable resin composition | Viscosity (mPa · s) | 11,400 | 11,800 | 11,600 | 9,500 | 95,000 | 45,000 | 54,000 | 68,000 | 10,200 |
| Evaluation of cured product | Abbe's number | 20.8 | 21.1 | 21.3 | 23.1 | 21.3 | 21.1 | 21.1 | 20.9 | 23.0 |
| | Crack resistance (time (h) until cracks occurred after storage at −40° C.) | 280 | 800 | 1200 | 500 | 150 | 30 | 100 | 20 | 450 |

TABLE 2

| | | Example 13 | Example 14 | Example 15 | Example 16 | Example 17 |
|---|---|---|---|---|---|---|
| Compound | Compound 2-1 | | | | | 35 |
| | Compound 2-1B | 50 | | | | 30 |
| | Compound 2-2B | | 40 | | | |
| | Compound 2-5B | | | 50 | | |
| | Compound 2-6B | | | | 50 | |
| | Substituent constant $\sigma_p$ values of $R^1$ to $R^4$ | −0.28 | −0.28 | −0.28 | −0.28 | −0.28 |
| (Meth)acrylate monomer | Monomer 1 | 43.7 | 53.7 | 43.7 | 43.7 | 28.7 |
| | Monomer 2 | | | | | |
| | Monomer 3 | | | | | |
| | Monomer 4 | | | | | |
| Non-conjugated vinylidene group-containing compound | β-caryophyllene | 4.5 | 4.5 | 4.5 | 4.5 | 4.5 |
| Photoradical polymerization initiator | Irgacure 651 | 0.1 | 0.1 | 0.1 | 0.1 | 0.1 |
| Thermal radical polymerization initiator | PERBUTYL O | 1 | 1 | 1 | 1 | 1 |
| | PERCUMYL H-80 | 0.7 | 0.7 | 0.7 | 0.7 | 0.7 |
| Evaluation of curable resin composition | Viscosity (mPa · s) | 7,800 | 7,400 | 8,100 | 8,200 | 13,000 |
| Evaluation of cured product | Abbe's number | 21.2 | 20.8 | 21.5 | 21.8 | 20.5 |
| | Crack resistance (time (h) until cracks occurred after storage at −40° C.) | 800 | 600 | 600 | 500 | 1,200 |

From Tables 1 and 2, it has been demonstrated that the curable composition of the present invention exhibits suppression of viscosity increase. Further, it has been demonstrated that the cured product prepared using the curable composition of the present invention has a low Abbe's number and excellent crack resistance (durability). On the other hand, it has been demonstrated that the evaluation results of at least one of the viscosity of the curable composition, the Abbe's number of the cured product, or the crack resistance (durability) are inferior in the curable compositions prepared using Comparative Compounds.

What is claimed is:

1. A curable composition, comprising:
a compound represented by General Formula (A);
a (meth)acrylate monomer having a viscosity at 25° C. of less than 2,000 mPa·s; and
at least one selected from a photoradical polymerization initiator and a thermal radical polymerization initiator, General Formula (A)

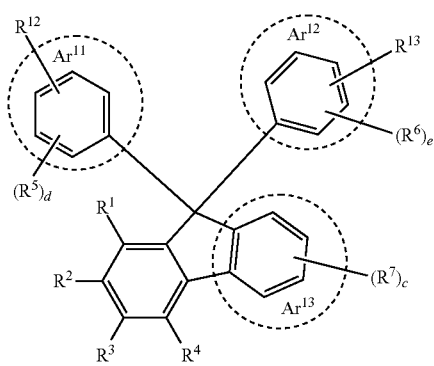

in General Formula (A), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $R^{12}$ and $R^{13}$ are each independently a hydroxyl group, a mercapto group, an amino group, or a group having a polymerizable unsaturated bond; c to e each independently represent an integer of 0 to 4; in a case where $Ar^{11}$ and $Ar^{12}$ are each independently an aromatic fused ring group containing a benzene ring surrounded by a broken line as one of the fused rings, $R^5$, $R^6$, $R^{12}$, and $R^{13}$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

2. The curable composition according to claim 1, wherein the compound is a compound represented by General Formula (1), General Formula (1)

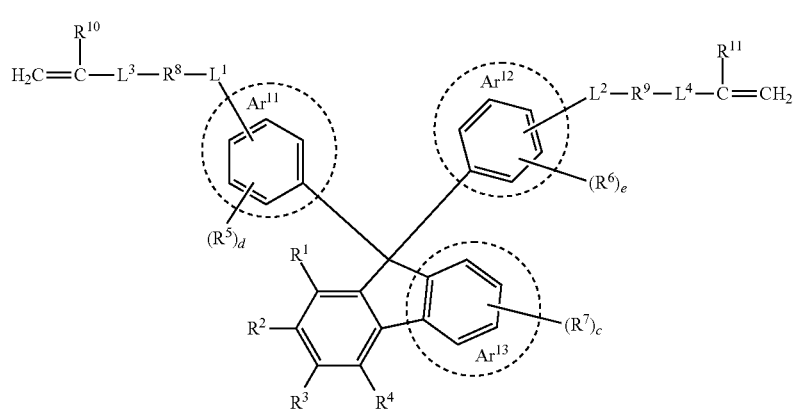

in General Formula (1), at least one of $R^1$, $R^2$, $R^3$, or $R^4$ is a substituent having a Hammett substituent constant $\sigma_p$ value of smaller than $-0.15$, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; in the case where $Ar^{11}$ and $Ar^{12}$ each independently represent an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

3. The curable composition according to claim 1, wherein the compound is a compound represented by General Formula (2), General Formula (2)

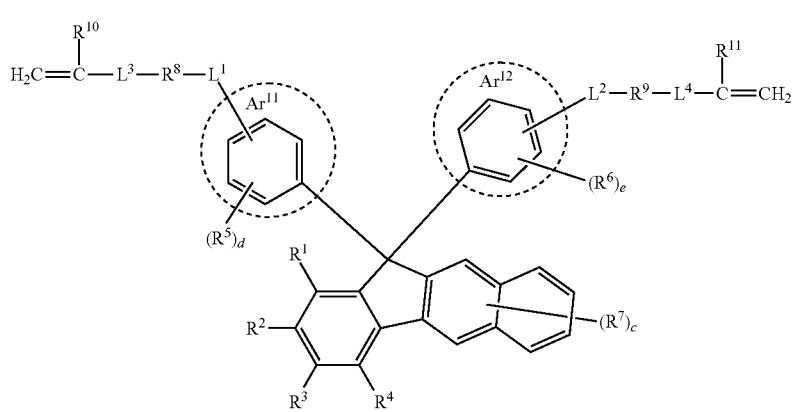

in General Formula (2), at least one of $R^1$, $R^2$, $R^3$, or $R^4$ is a substituent having a Hammett substituent constant $\sigma_p$ value of smaller than $-0.15$, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; and in the case where $Ar^{11}$ and $Ar^{12}$ are each independently an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line.

4. The curable composition according to claim 1, wherein at least one of $R^2$ or $R^4$ is a substituent having a Hammett substituent constant $\sigma_p$ value of smaller than −0.15.

5. The curable composition according to claim 1, wherein at least one of $R^1$, $R^2$, $R^3$, or $R^4$ is an alkyl group, an alkoxy group, or a dialkylamino group.

6. The curable composition according to claim 1, wherein at least one of $R^1$, $R^2$, $R^3$, or $R^4$ is an alkoxy group.

7. The curable composition according to claim 1, wherein at least one of $R^2$ or $R^4$ is an alkoxy group.

8. The curable composition according to claim 1, wherein at least one of $R^2$ or $R^4$ is an alkoxy group, and at least two of $R^1$, $R^2$, $R^3$, or $R^4$ are alkoxy groups.

9. The curable composition according to claim 1, wherein $R^2$ and $R^3$ are alkoxy groups.

10. The curable composition according to claim 5, wherein the alkoxy group is a methoxy group.

11. The curable composition according to claim 1, wherein the viscosity at 25° C. of the (meth)acrylate monomer is less than 500 mPa·s.

12. The curable composition according to claim 1, wherein the (meth)acrylate monomer is a (meth)acrylate monomer containing an aryl group or a heteroaryl group.

13. The curable composition according to claim 1,
   wherein the content of the compound in the curable composition is 20 to 94 mass %,
   the content of the (meth)acrylate monomer is 5 to 80 mass %, and
   the content of at least one selected from a photoradical polymerization initiator and a thermal radical polymerization initiator is 0.01 to 10 mass %.

14. A cured product of the curable composition according to claim 1.

15. An optical component comprising the cured product according to claim 14.

16. A lens comprising the cured product according to claim 14.

17. A compound represented by General Formula (A),

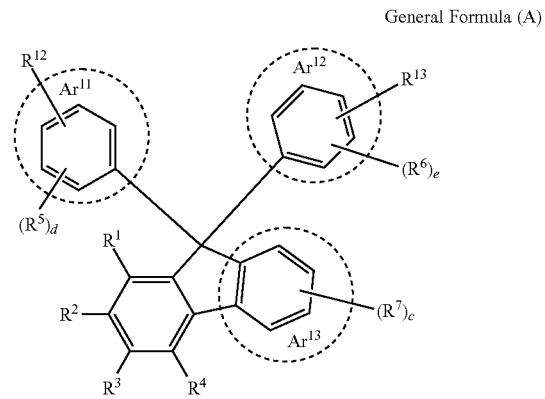

General Formula (A)

in General Formula (A), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $R^{12}$ and $R^{13}$ are each independently a hydroxyl group, a mercapto group, an amino group, or a group having a polymerizable unsaturated bond; c to e each independently represent an integer of 0 to 4; in a case where $Ar^{11}$ and $Ar^{12}$ are each independently an aromatic fused ring group containing a benzene ring surrounded by a broken line as one of the fused rings, $R^5$, $R^6$, $R^{12}$, and $R^{13}$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

18. The compound according to claim 17, wherein the compound is represented by General Formula (1), General Formula (1)

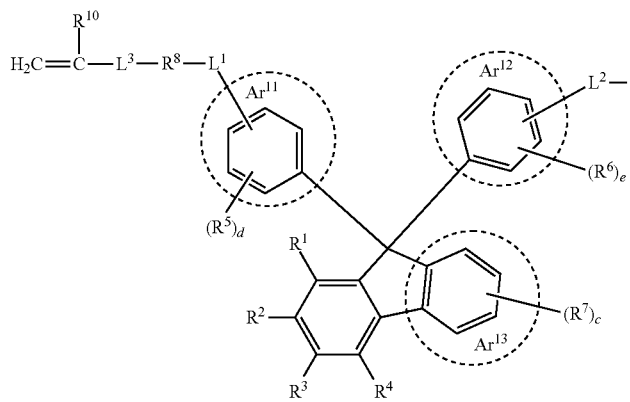

in General Formula (1), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line, and $Ar^{13}$ is an aromatic fused ring group containing a benzene ring surrounded by a broken line as one of the fused rings; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; in the case where $Ar^{11}$ and $Ar^{12}$ each independently represent an aromatic fused ring group containing a benzene ring surrounded by a broken line as one of the fused rings, a group having L as a linking group, a group having $L^2$ as a linking group, $R^5$, and $R^6$ may each independently be substituted with a benzene ring surrounded by a broken line or may be substituted with a fused ring other than a benzene ring surrounded by a broken line; and $R^7$ may be substituted with a benzene ring surrounded by a broken line or may be substituted with a fused ring other than a benzene ring surrounded by a broken line.

19. The compound according to claim 17, wherein the compound is represented by General Formula (2), General Formula (2)

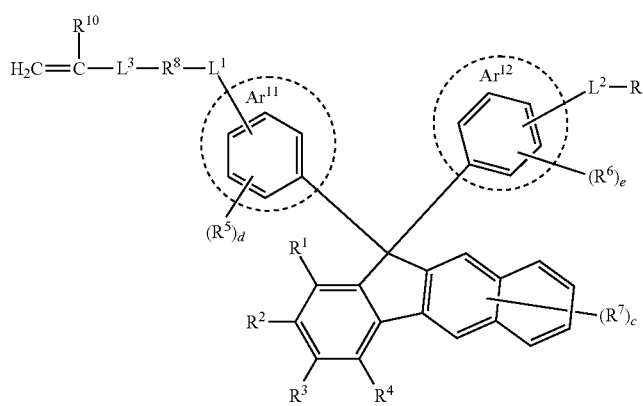

in General Formula (2), at least one of $R^1$, $R^2$, $R^3$, or $R^4$ is a substituent having a Hammett substituent constant $\sigma_p$ value of smaller than −0.15, provided that $R^1$ to $R^4$ are each independently a substituent having no reactive group, and $R^1$ to $R^4$ substituents adjacent to each other are not bonded to each other to form a fused ring; $R^5$ to $R^7$ each independently represent a substituent; $Ar^{11}$ and $Ar^{12}$ each independently represent an aryl group containing a benzene ring surrounded by a broken line or a heteroaryl group containing a benzene ring surrounded by a broken line; $L^1$ and $L^2$ each independently represent a single bond, an oxygen atom, or a sulfur atom, $R^8$ and $R^9$ each independently represent a linking group containing at least one selected from an ether bond, an ester bond, a thioether bond, a thioester bond, an amide bond, a carbonate bond, and an alkylene group, or a single bond, $L^3$ and $L^4$ each independently represent a single bond, an ester bond, a thioester bond, or an amide bond, and $R^{10}$ and $R^{11}$ each independently represent a hydrogen atom or a methyl group; c to e each independently represent an integer of 0 to 4; and in the case where $Ar^{11}$ and $Ar^{12}$ are each independently an aromatic fused ring group containing a benzene ring surrounded by a broken line as one of the fused rings, a group having $L^1$ as a linking group, a group having $L^2$ as a linking group, $R^5$, and $R^6$ may each independently be substituted with a benzene ring surrounded by a broken line or may be substituted with a fused ring other than a benzene ring surrounded by a broken line.

20. The compound according to claim 17, wherein at least one of $R^1$, $R^2$, $R^3$, or $R^4$ is an alkyl group, an alkoxy group, or a dialkylamino group.

21. The compound according to claim 17, wherein at least one of $R^1$, $R^2$, $R^3$, or $R^4$ is an alkoxy group.

22. The compound according to claim 17, wherein at least one of $R^2$ or $R^4$ is an alkoxy group.

23. The compound according to claim 17, wherein at least one of $R^2$ or $R^4$ is an alkoxy group, and at least two of $R^1$, $R^2$, $R^3$, or $R^4$ are alkoxy groups.

24. The compound according to claim 17, wherein $R^2$ and $R^3$ are alkoxy groups.

25. The compound according to claim 20, wherein the alkoxy group is a methoxy group.

* * * * *